United States Patent
Mamo et al.

(10) Patent No.: US 6,847,849 B2
(45) Date of Patent: Jan. 25, 2005

(54) MINIMALLY INVASIVE APPARATUS FOR IMPLANTING A SACRAL STIMULATION LEAD

(75) Inventors: George Mamo, Ellicott City, MD (US); Michele Spinelli, Milan (IT); John Matthew Swoyer, Andover, MN (US); Martin Theodore Gerber, Maple Grove, MN (US); Keith Richard Carlton, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/827,740

(22) Filed: Apr. 7, 2001

(65) Prior Publication Data

US 2002/0147485 A1 Oct. 10, 2002

Related U.S. Application Data

(63) Continuation-in-part of application No. 09/713,598, filed on Nov. 15, 2000.

(51) Int. Cl.[7] .................................................. A61N 1/00
(52) U.S. Cl. ..................................................... 607/117
(58) Field of Search ........................ 607/115, 117, 607/118; 604/164.01–170.03; 606/185

(56) References Cited

U.S. PATENT DOCUMENTS

| | | |
|---|---|---|
| 4,044,774 A | 8/1977 | Corbin et al. |
| 4,512,351 A | 4/1985 | Pohndort |
| 4,569,351 A | 2/1986 | Tang |
| 4,573,448 A * | 3/1986 | Kambin .................... 606/170 |
| 4,607,639 A | 8/1986 | Tanagho et al. |
| 4,739,764 A | 4/1988 | Lue et al. |
| 4,771,779 A | 9/1988 | Tanagho et al. |
| 5,121,754 A | 6/1992 | Mullet |
| 5,255,691 A | 10/1993 | Otten |
| 5,395,317 A * | 3/1995 | Kambin .................... 604/506 |

(List continued on next page.)

OTHER PUBLICATIONS

Medtronic, "InterStim® Therapy, Sacral Nerve Stimulation For Urinary Control, Therapy Reference Guide," (1999).

(List continued on next page.)

Primary Examiner—Mark Bockelman
(74) Attorney, Agent, or Firm—Thomas F. Woods; Keith M. Campbell

(57) ABSTRACT

Methods and apparatus for implanting a stimulation lead in a patient's sacrum to deliver neurostimulation therapy that can reduce patient surgical complications, reduce patient recovery time, and reduce healthcare costs. A surgical instrumentation kit for minimally invasive implantation of a sacral stimulation lead through a foramen of the sacrum in a patient to electrically stimulate a sacral nerve comprises a needle and a dilator and optionally includes a guide wire. The needle is adapted to be inserted posterior to the sacrum through an entry point and guided into a foramen along an insertion path to a desired location. In one variation, a guide wire is inserted through a needle lumen, and the needle is withdrawn. The insertion path is dilated with a dilator inserted over the needle or over the guide wire to a diameter sufficient for inserting a stimulation lead, and the needle or guide wire is removed from the insertion path. The dilator optionally includes a dilator body and a dilator sheath fitted over the dilator body. The stimulation lead is inserted to the desired location through the dilator body lumen or the dilator sheath lumen after removal of the dilator body, and the dilator sheath or body is removed from the insertion path. If the clinician desires to separately anchor the stimulation lead, an incision is created through the entry point from an epidermis to a fascia layer, and the stimulation lead is anchored to the fascia layer. The stimulation lead can be connected to the neurostimulator to delivery therapies to treat pelvic floor disorders such as urinary control disorders, fecal control disorders, sexual dysfunction, and pelvic pain.

13 Claims, 34 Drawing Sheets

U.S. PATENT DOCUMENTS

| | | | |
|---|---|---|---|
| 5,484,445 A | | 1/1996 | Knuth |
| 5,733,322 A | | 3/1998 | Starkebaum |
| 5,762,629 A | * | 6/1998 | Kambin ................. 604/164.11 |
| 5,957,965 A | | 9/1999 | Moumane et al. |
| 6,002,964 A | | 12/1999 | Feler et al. |
| 6,027,456 A | | 2/2000 | Feler et al. |
| 6,055,456 A | | 4/2000 | Gerber |
| 6,104,957 A | | 8/2000 | Alo et al. |
| 6,104,960 A | | 8/2000 | Duysens et al. |
| 6,360,750 B1 | * | 3/2002 | Gerber et al. ................ 128/898 |
| 6,395,007 B1 | * | 5/2002 | Bhatnagar et al. ............ 606/94 |

OTHER PUBLICATIONS

Medtronic "InterStim® Therapy, SNS For Urinary Control, Test Stimulation And Implantation Guide," (1999).

Medtronic, Implantable Neurostimulation Systems Brochure, (1998).

Medtronic, "InterStim® Therapy, Sacral Nerve Stimulation (SNS) For Urinary Control, 1999 Compendium of Key Abstracts," (1999).

Anurag, K. Das et al., "Sacral Nerve Stimulation For The Management Of Voiding Dysfunction," Reviews In Urology, vol. 1, Issue 46 (Winter 2000). pp 43–60.

J. Bosch et al., "Sacral Nerve Neuromodulation In The Treatment Of Patients With Refractory Motor Urge Incontinence: Long–Term Results Of A Prospective Longitudinal Study," *The Journal Of Urology*, vol. 163, No. 4 (Apr. 2000). pp 1219–1222.

Hassouna, M. et al., "Sacral Neuromodulation In The Treatment Of Urgency–Frequency Symtoms: A Multicenter Study On Efficacy And Safety," *The Journal Of Urology*, vol. 163, No. 6 (Jun. 2000). pp 1849–1854.

Schmidt, R. et al., "Sacral nerve Stimulation For Treatment Of Refractory Urinary Urge Incontinence," *The Journal Of Urology*, vol. 162, No. 2 (Aug. 1999).

* cited by examiner

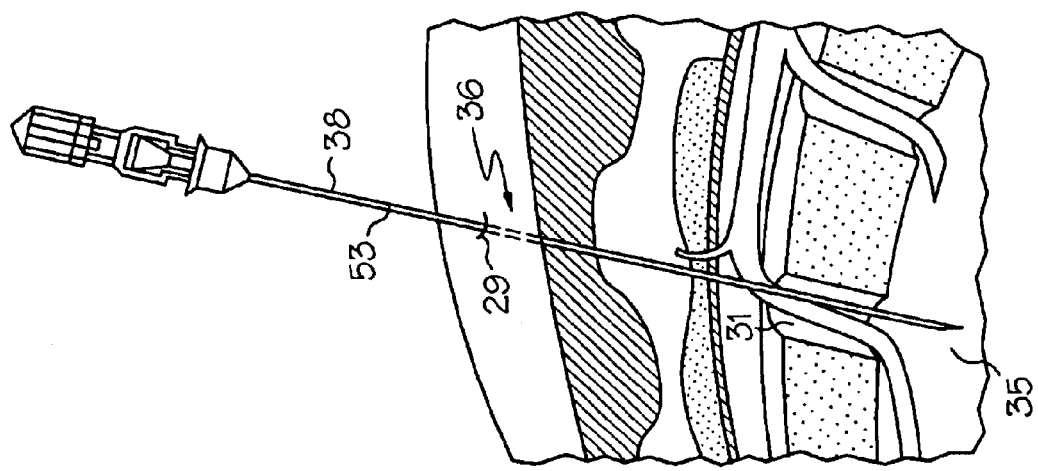
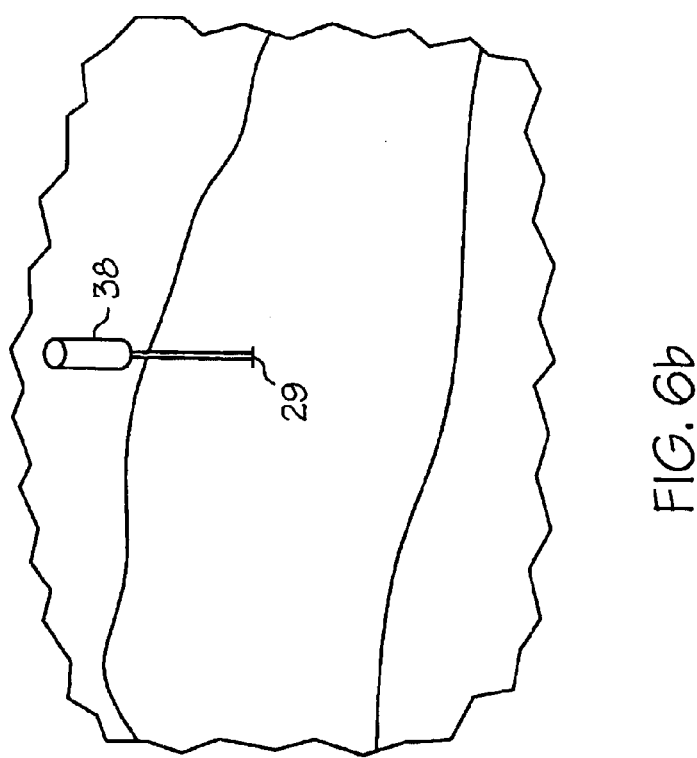

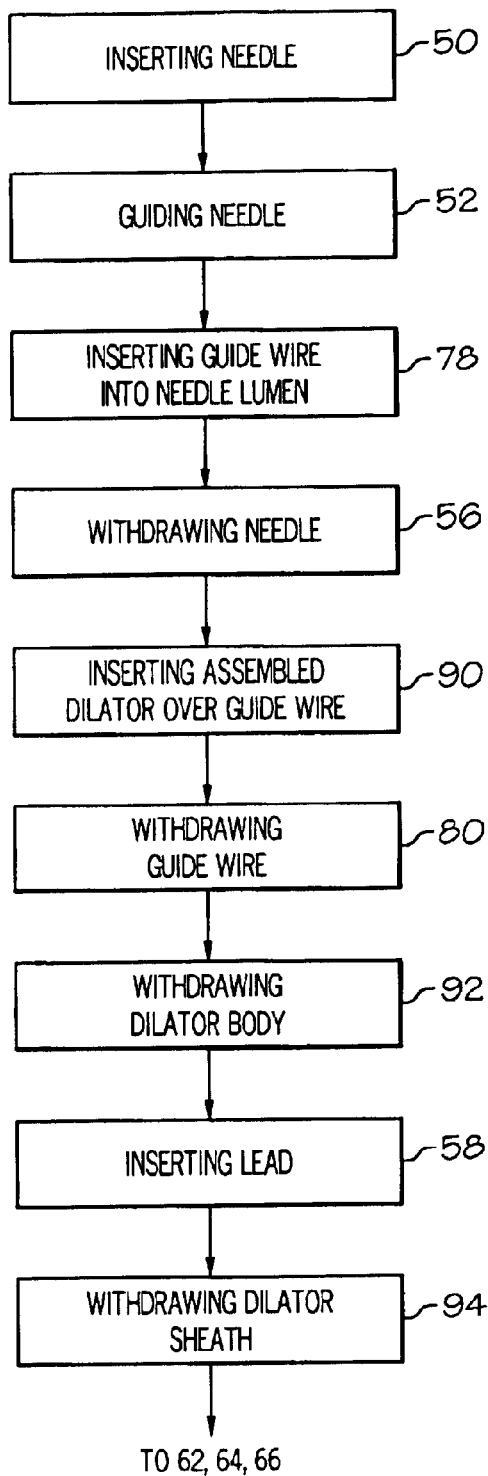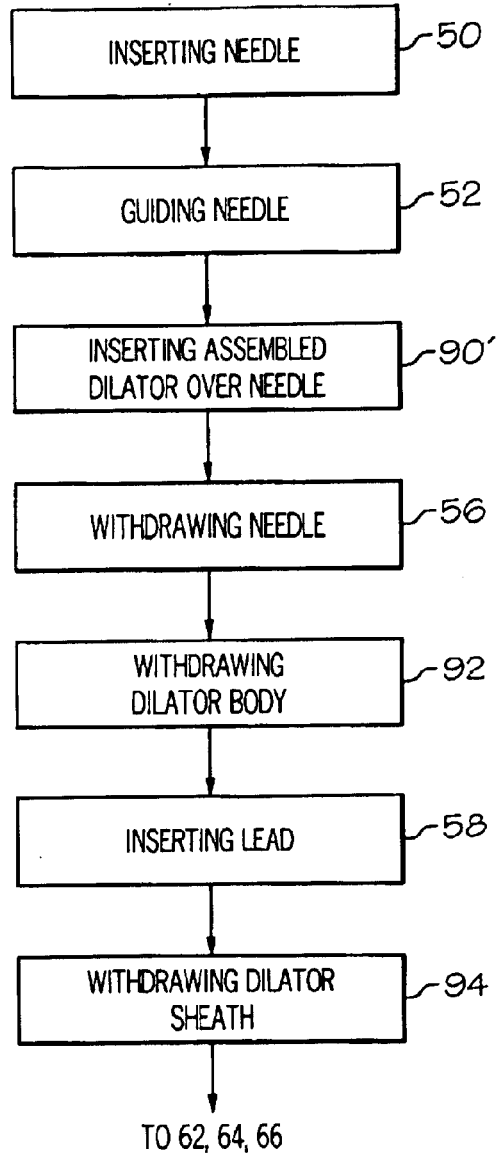
FIG. 9a
FIG. 10

MINIMALLY INVASIVE APPARATUS FOR IMPLANTING A SACRAL STIMULATION LEAD

This is a continuation-in-part of U.S. patent application Ser. No. 09/713,598 filed Nov. 15, 2000 for MINIMALLY INVASIVE METHOD FOR IMPLANTING A SACRAL STIMULATION LEAD.

CROSS REFERENCE

This disclosure is related to the following co-pending application entitled "Minimally Invasive Surgical Techniques For Implanting Devices That Deliver Stimulation To The Nervous System" by inventors Gerber et al. (application Ser. No. 09/489,544; filed Jan. 31, 2000), which is not admitted as prior art with respect to the present disclosure by its mention in this cross-reference section.

BACKGROUND OF THE INVENTION

This disclosure relates to apparatus in the form of a kit of medical instruments used for surgically implanting an electric neurostimulation lead in the human sacrum.

The medical device industry produces a wide variety of electronic and mechanical devices for treating patient medical conditions. Depending upon the medical condition, medical devices can be surgically implanted or connected externally to a patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Conditions that medical devices can effectively treat include pelvic floor disorders.

Pelvic floor disorders adversely affect the health and quality of life of millions of people. Pelvic floor disorders include urinary control disorders such as urge incontinency, urge frequency, voiding efficiency, fecal control disorders, sexual dysfunction, and pelvic pain. Individuals with urinary control disorders often face debilitating challenges in their everyday lives. These individuals can be preoccupied with trips to the bathroom, fears of embarrassment, and sleepless nights. Some suffers become so anxious that they become isolated and depressed. Pelvic floor disorders can be treated with a variety of therapeutic options such as behavior modification including biofeedback, pharmacological treatment, mechanical intervention such as self-catheterization, physical appliances such as diapers, and surgical intervention. Surgical treatments are the most invasive and are often considered after other therapies have proven ineffective.

One surgical technique to treat urinary control disorders is the implantable InterStim® therapy, available from Medtronic, Inc., which applies mild electrical stimulation to the sacral nerves in the lower region of the spine to influence behavior of structures such as the bladder, sphincter and pelvic floor muscles. Generally, implantation of InterStim therapy involves surgically implanting a stimulation lead near the sacral nerves. The stimulation lead is a very small, insulated electrical conductor with electrical stimulation contacts on the distal end placed near the sacral nerves and an electrical connector on the opposite proximal end of the lead. The lead electrical connector is typically connected to a small extension, and the extension is connected to a small neurostimulator that operates similar to a cardiac pacemaker by delivering occasional small electrical pulses that sometimes create a tingling sensation felt by the patient. The stimulation lead, lead extension, and neurostimulator are all implanted in the patient in a manner that is typically not perceptible by others. InterStim therapy can improve the condition of a pelvic floor disorder patient and allow the patient to lead a full life. Also, InterStim therapy is nondestructive and reversible.

Previous surgical methods and apparatus used to implant a neurostimulation lead in a patient's sacrum to treat pelvic floor disorders have been invasive by requiring a large sacral incision in a procedure known as dissection. FIG. 1a (prior art) shows a sacral dissection. Dissection involves making a midline incision over the sacrum from a little below S4 up to S1 that in an adult ranges from about 7.62 cm (3.0 inches) to 12.7 cm (5.0 inches). After the incision is made, the fascia lateral to the midline is cleaned off and divided in the direction of the incision approximately one finger width lateral to the midline. Next, the paraspinal muscle fibers are split and sharply retracted. Once the muscle fibers are retracted, the sacral foramen is exposed while preserving the periosteum. Next, the desired foramen is located by observing anatomical landmarks and palpating for a marble-board-like depression in the posterior sacral surface. FIG. 1b (prior art) shows a foramen dissection. Once the desired foramen is located, another small incision is made over the desired foramen that is large enough to allow insertion of the stimulation lead. The stimulation lead is inserted through the incision. Surgically implanting the stimulation lead in this manner near the patient's sacral nerve can cause patient complications, create significant patient's recovery time, and create a significant expense to the healthcare system. An example of the previous surgical method to implant a neurostimulation lead is described in Medtronic, "InterStim® Therapy Sacral Nerve Stimulation For Urinary Control Therapy Reference Guide," Section 5 InterStim Device Implantation Procedure, pp. 51–52 (1999).

For the foregoing reasons, there is a need for a less invasive surgical instrument set for performing a method of implanting a neurostimulation lead in a patient through a foramen of the sacrum in relation to a sacral nerve, whereby patient surgical complications, surgical recovery time, and surgical costs are reduced while maintaining the substantial patient benefits of neurostimulation of the sacral nerve.

SUMMARY OF THE INVENTION

The minimally invasive instrument set for implanting sacral stimulation leads comprises at least a needle and a dilator that are particularly adapted to enable introduction of a neurostimulation lead into a foramen to locate a distal neurostimulation lead electrode(s) in operative relation to a sacral nerve. The needle is adapted to be grasped by a medical clinician with the needle distal end directed toward and inserted through an entry point of the skin or a skin incision posterior to the sacrum and guided along an insertion path into a foramen to locate at least a distal portion of the needle extending alongside a sacral nerve and a proximal portion of the needle extending from the entry point away from the patient's skin. The dilator is adapted to be inserted over the needle proximal end to locate the needle within the dilator body lumen and to be advanced distally over the needle through the insertion path to dilate the insertion path to the dilator diameter. The needle is adapted to be withdrawn through the dilator body lumen so that the stimulation lead can be advanced through the dilator body lumen to locate the stimulation lead electrode into operative relation to the sacral nerve. The dilator is adapted to be withdrawn over the stimulation lead body.

Alternatively, the minimally invasive instrument set comprises a needle having a needle lumen, a dilator and a guide wire that are particularly adapted to enable introduction of a neurostimulation lead into a foramen. The guide wire has a guide wire diameter sized to fit through the needle lumen and a guide wire length extending between a guide wire proximal end and a guide wire distal end. The guide wire is adapted to be inserted through the needle lumen to locate a distal portion of the guide wire through the foramen of the sacrum after the needle is guided into position. The needle is adapted to be withdrawn over the guide wire, and the dilator is adapted to be inserted over the guide wire proximal end to locate the guide wire within the dilator body lumen and to be advanced distally over the guide wire through the insertion path to dilate the insertion path to the dilator diameter. The guide wire is adapted to be withdrawn through the dilator body lumen, the stimulation lead is adapted to be advanced through the dilator body lumen to locate the stimulation lead electrode into operative relation to the sacral nerve, and the dilator is adapted to be withdrawn over the stimulation lead body.

In a further preferred embodiment, the dilator comprises the assembly of a dilator body and a dilator sheath that are inserted through the skin as an assembly and are separated to enable introduction of the neurostimulation lead through the dilator sheath lumen. The dilator is adapted to be introduced over the needle or guide wire as above described, whereupon the dilator body and guide wire are withdrawn, leaving the dilator sheath. The stimulation lead is adapted to be advanced through the dilator body lumen to locate the stimulation lead electrode into operative relation to the sacral nerve, and the dilator sheath is adapted to be withdrawn over the stimulation lead body.

The needle, dilator and guide wire are all preferably formed of a conductive material insulated along the exposed lengths thereof but exposed at or along the proximal and distal ends thereof so as to be capable of being used to conduct test stimulation to the sacral nerve to assess the efficacy of stimulation prior to implantation of the neurostimulation lead and to establish the depth of positioning of the neurostimulation lead electrode.

The needle, dilator, guide wire and neurostimulation lead bodies are marked with depth indicators that are correlated to one another so that the depth of insertion from the skin of each is ascertainable from the exposed marking so as to assure that the clinician extends each instrument to the same depth to properly locate the neurostimulation lead electrode in operative relation to the sacral nerve.

The guide wire may be relatively stiff to prevent bending or flexible to enable a degree of bending.

Additionally if the clinician desires to separately anchor the stimulation lead, an incision can be created through the entry point from an epidermis to a fascia layer. The stimulation lead is anchored to the fascia layer. Finally, the incision is closed. The minimally invasive instrumentation set and method of sacral stimulation lead implantation can be practiced in a wide variety of embodiments.

BRIEF DESCRIPTION OF THE DRAWINGS

FIG. 6b shows a patient having a needle inserted posterior to the patient sacrum embodiment;

FIG. 6c shows an anatomical drawing of the needle inserted as shown in the FIG. 6b embodiment;

FIG. 6l shows removal of the dilator embodiment;

FIG. 9a shows a flowchart of a fifth minimally invasive method embodiment employing the dilator of FIGS. 8a–8c along with the needle of FIGS. 3a or 3d;

FIG. 10 shows a flowchart of a sixth minimally invasive method embodiment employing the dilator of FIGS. 8a–8c along with the needle of FIGS. 3a or 3d.

DETAILED DESCRIPTION OF THE PREFERRED EMBODIMENTS

Figure 1A:
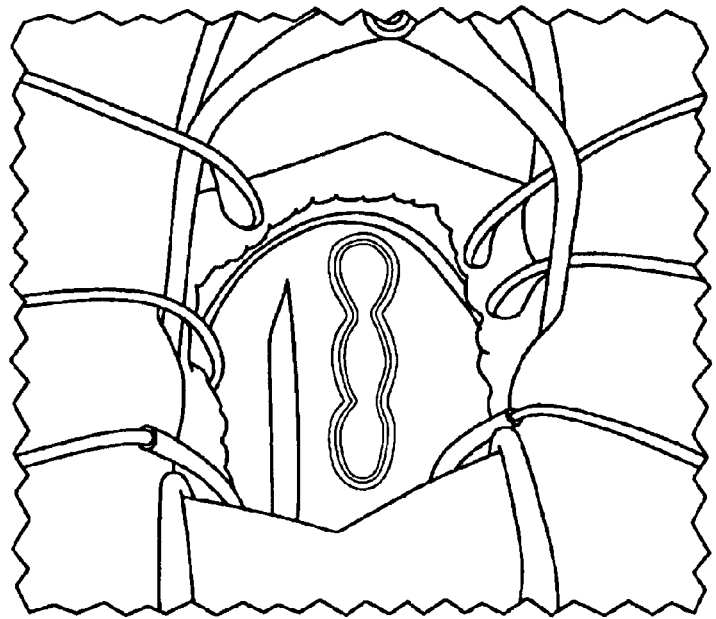
FIG. 1a shows a prior art sacral dissection.
Figure 1B:
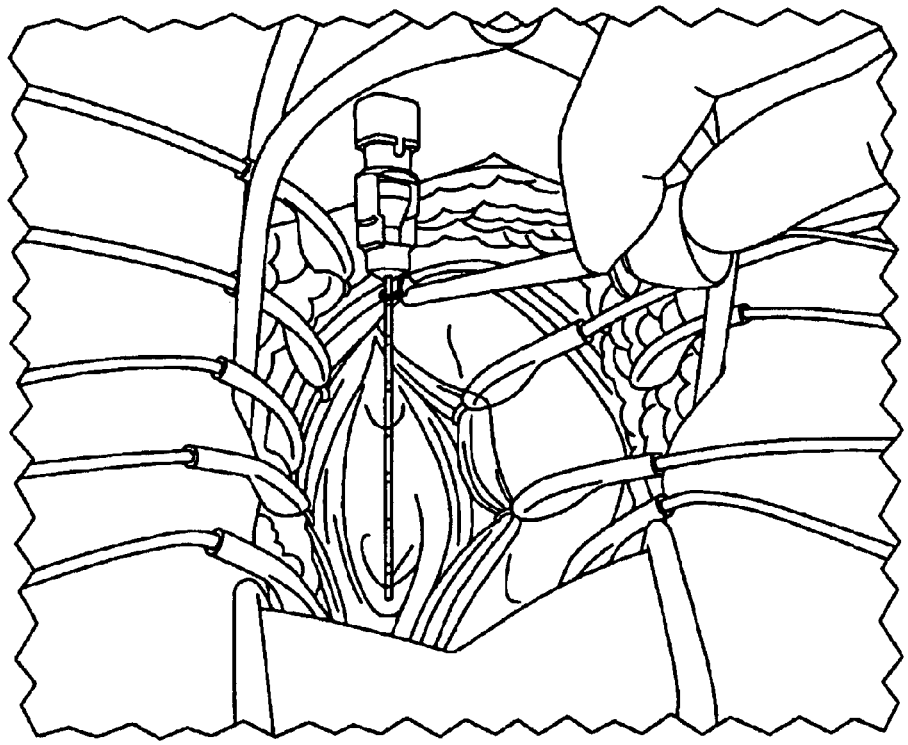
FIG. 1b shows a prior art foramen dissection.
Figure 1C:
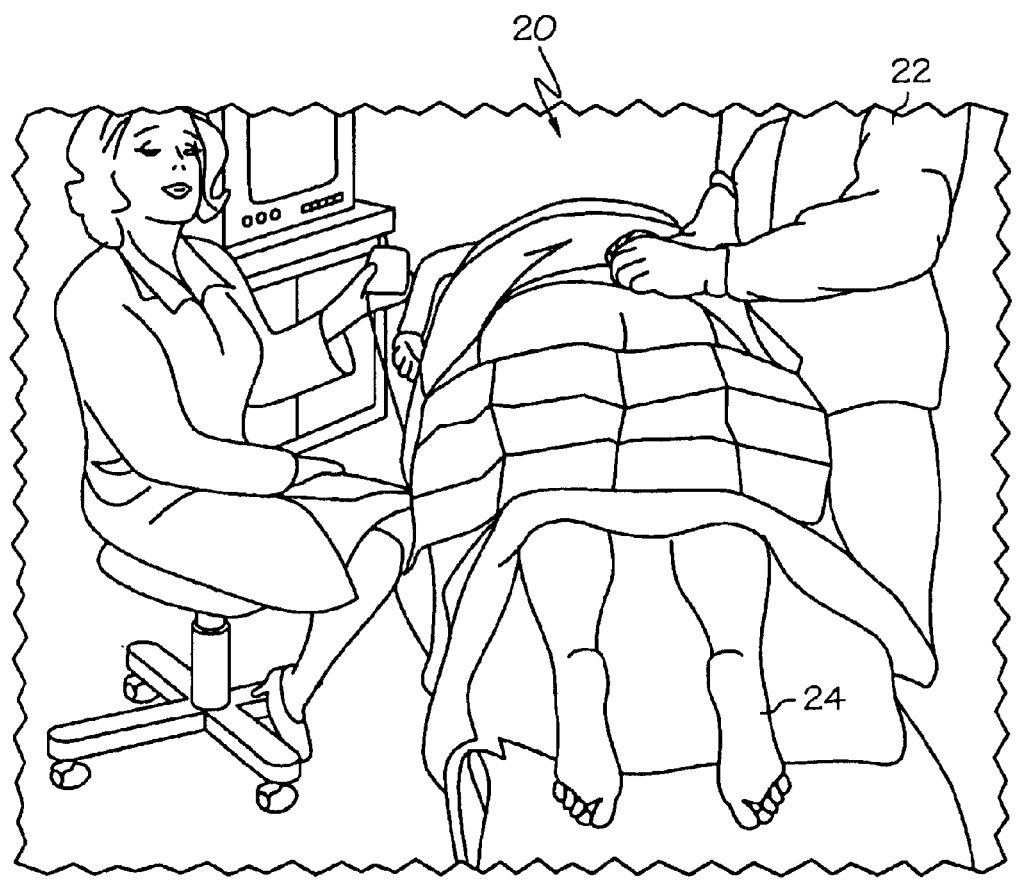
FIG. 1c shows an environment of a patient undergoing a sacral stimulation procedure.

FIG. 1c shows an environmental view of a sterile area in which the minimally invasive method for implanting a sacral stimulation lead can be performed. The method can be performed in a wide variety of locations 20 that have a sterile field and common medical instruments such as an operating room, surgery center. The method and its many embodiments are typically performed by a urologist 22, but can be performed by many clinicians 22 trained in stimulation lead implantation. The patient 24 is placed under local or general anesthesia. With local anesthesia, the method can potentially be performed in a clinician's 22 office for greater accessibility and reduced costs. A sacral stimulation lead can be implanted for a variety a purposes such as to treat pelvic floor disorders. Pelvic floor disorders include urinary control disorders, fecal control disorders, sexual dysfunction, and pelvic pain.

Figure 2:
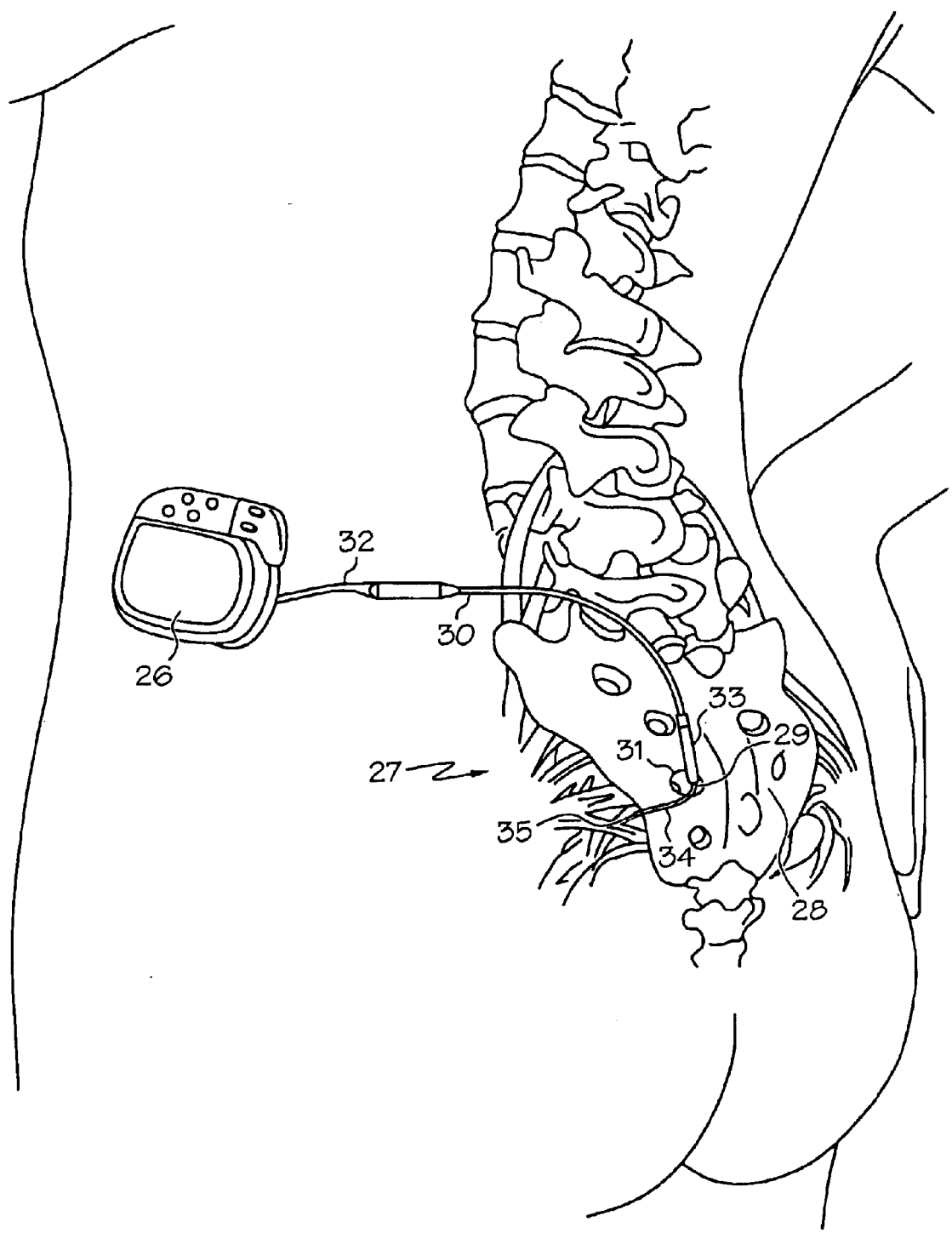
FIG. 2 shows an embodiment of an implanted neurostimulator.

FIG. 2 shows an embodiment of an implanted neurostimulator 26 to stimulate sacral nerves 27 located near the sacrum 28. The sacral nerves are assessable through an entry point 29 along an insertion path 33 into a foramen 31 to reach a desired location 35. A neurostimulation system can include a stimulation lead 30, a lead anchor (FIG. 3g), a lead extension 32, a trial stimulator (not shown), an implantable neurostimulator 26, a physician programmer (not shown), and a patient programmer (not shown). The stimulation lead 30 has electrical contacts 34 positioned on the distal end to stimulate nerves and connectors (not shown) on the proximal end to connect to a lead extension or directly to the trial neurostimulator or implantable neurostimulator 26. The stimulation lead 30 can be a Medtronic Model 3886 quadrapolar lead without anchor having a diameter of approximately a 0.127 cm (0.050 inch) and designed to accept a stylet through the center of the stimulation lead 30 to assist in insertion. The lead anchor (FIG. 3f) fixes the stimulation lead 30 to prevent the stimulation lead 30 from migrating away from the position selected by the implanting clinician 22. The lead extension 32 connects between the stimulation lead 30 and the trial stimulator or implantable stimulator 26. The trial neurostimulator tests the effectiveness of stimulation to treat the patient's condition prior to implantation of an implantable neurostimulator 26.

The implantable neurostimulator 26 provides a programmable stimulation signal that is delivered to a desired location or target to stimulate selected nerves. The implantable neurostimulator 26 is typically implanted in a subcutaneous pocket around the upper buttocks sometime after the stimulation lead 30 has been implanted and its effectiveness verified. The physician programmer is used by the clinician 22 to communicate with the implantable neurostimulator 26 to program the stimulation signal produced by the implantable neurostimulator. The patient programmer allows the patient to communicate with the implantable neurostimulator to control certain parameters of the stimulation signal typically selected by a clinician. With a pelvic floor disorder, a patient can typically control stimulation signal parameters such as voltage amplitude. Neurostimulation systems with the components discussed above are available from Medtronic, Inc. in Minneapolis, Minn.

FIGS. 3a–3g show some of the surgical instruments (not to scale) typically available to the implanting clinician to aid in implanting the stimulation lead 30, the instruments selected to form instrument kits of the present invention. Local anesthetic is delivered to the patient typically with a syringe such as a Luer Slip Disposable 12 cc syringe (not shown). The needle 36 is selected based upon the needs of the patient 24 typically ranging in size from an outer diameter of about 26 gauge (0.46 mm) to about 12 gauge (2.80 mm) such as the 20 gauge (0.89 mm), thin wall, foramen needle 38 Models 041828 and 041829 available from Medtronic. The foramen needle 38 has a stylet 40, also known as an obturator, in the foramen needle 38 central opening and markings that measure 1.0 cm increments and a wider mark at 5.0 cm to aid in positioning needle depth. Additionally the foramen needle 38 tip and proximal portion adjacent to the hub are conductive, so a trial stimulator can be electrically connected to the hub. The trial stimulator stimulation signal will travel to the foramen needle 38 tip to evoke a response from the patient 24 to determine if the foramen needle 38 is properly position and whether the patient 24 will likely benefit from stimulation.

The dilators 42 can be metal or plastic dilators typically ranging in size from an outer diameter of about 5 French (0.33 mm) to about 14 French (4.00 mm), such as an Angiocath® intravenous catheter placement unit available from Parke Davis & Company, selected based upon the size of stimulation lead 30 to be implanted. Multiple dilators 42 can be used typically in sequence from a smaller diameter to a larger diameter to achieve the desired dilation while controlling tissue trauma. The guide wire 44 is typically a thin biocompatible stainless steel wire with a diameter such as 0.076 cm (0.030 inch). Dilators 42 and guide wires 44 are available in cardiac pacing lead introducer kits such as Medtronic's Model 3208, Percutaneous Lead Introducer. The dilator 42 can be a metal or plastic dilator sized appropriately to pass the stimulation lead 30 such as an 8 French (2.6 mm) sized dilator. The neurostimulation lead anchor 46 shown in FIG. 3g over stimulation lead 30 is an implantable surgical anchor configured to fix to the stimulation lead 30 such as a suture anchor or a twist-lock anchor available in the Medtronic Model 3550-1 Boots and Anchors Accessory Kit or the silicone anchor included in the Medtronic Model 3886 Lead Electrode Kit. Additionally to assist the clinician 22 in guiding placement of the needle 36 and guide wire 44, the clinician 22 may use a fluoroscope or x-ray machine.

First Minimally Invasive Method Embodiment

Figure 3A:
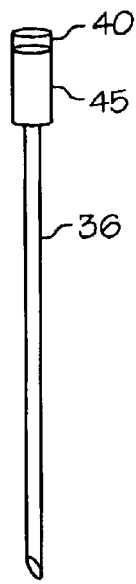
FIGS. 3a–3g show some surgical tools that can be used to perform the minimally invasive method.
Figure 3B:
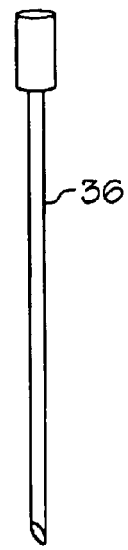
Figure 3C:
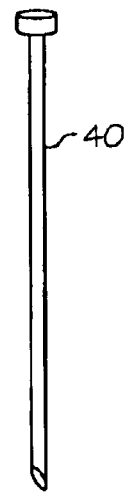
Figure 3D:
Figure 3E:
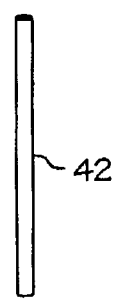
Figure 3F:
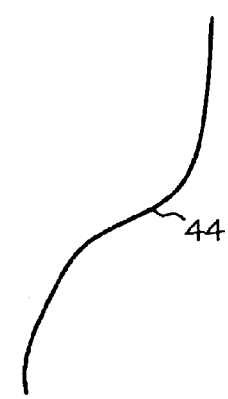
Figure 3G:
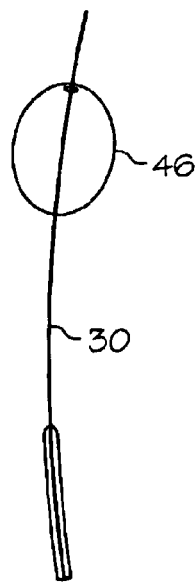
Figure 4:
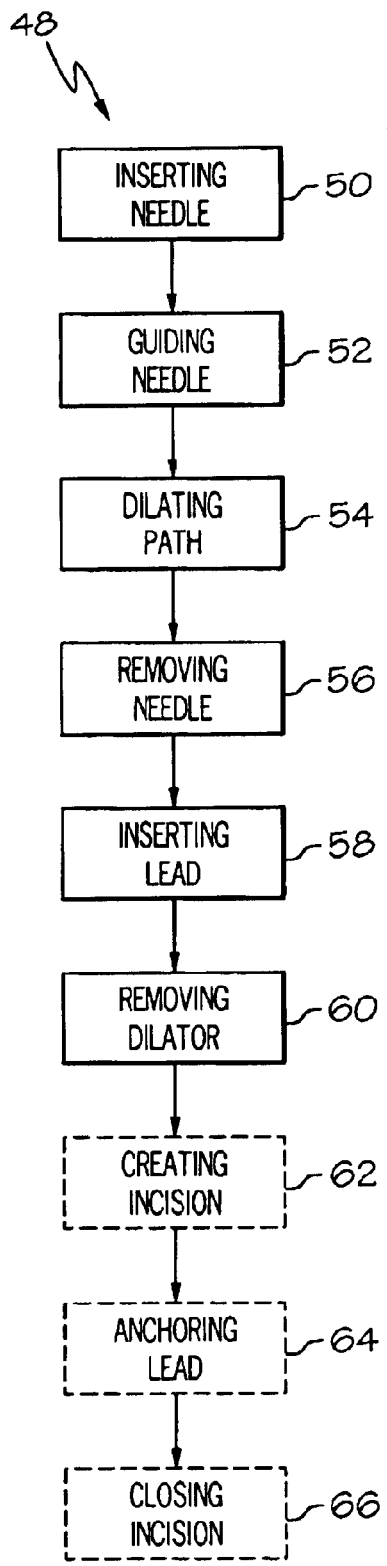
FIG. 4 shows a flowchart of a first minimally invasive method embodiment.

FIG. 4 shows a flowchart of a first embodiment of the minimally invasive implantation method employing a first instrument kit of the present invention. FIG. 2 shows an embodiment of an implanted neurostimulator 26 to stimulate sacral nerves 27, and FIGS. 3a–3g show some surgical tools that can be used to perform the minimally invasive method. Prior to beginning the first method for minimally invasive method embodiment 48 for sacral electrical stimulation lead 30 implantation in a patient 24, the following preparatory actions are typically taken. A local anesthetic is typically applied to anesthetize the area where the stimulation lead 30 will be implanted such as posterior to the sacrum 28. Since embodiments of the method permit use of a local anesthetic, patients 24 can be treated on an outpatient basis to greatly reduces costs over inpatient care and reduce recovery time. This significant cost reduction also makes sacral stimulation lead 30 implantation and its many beneficial therapies available to more patients 24 because healthcare payers are more likely to cover procedure costs. Also by using local anesthesia, the implanting clinician 22 can use the patient's 24 conscious sensory response to stimuli such as trial stimulation to aid in placing the stimulation lead 30. By using the patient's 24 conscious sensory response during stimulation lead 30 placement, the stimulation lead 30 can be more accurately placed reducing the potential for an ineffective therapy and reducing the potential for patient 24 injury caused by a misplaced lead 30. Other forms of anesthesia can also be used such as general anesthesia. Once the patient 24 has been anesthetized, the first method embodiment 48 can begin.

A needle 36 is inserted 50 posterior to the sacrum 28 through an entry point 29 typically created with the needle 36. The needle 36 can take a variety of forms such as a needle without a hub (cannula), a solid rod with a sharp tip, a needle with a hub that can be removed for example by a cutting tool, or a foramen needle 38 modified to have an extended length and a hub that can be removed with a cutting tool. The entry point 29 is typically a percutaneous entry created when the needle 36 is inserted. The needle 36 is hand guided 52 into the foramen 31 along an insertion path 33 to a desired location 35. The foramen's 31 approximate location can be found using anatomical landmarks, fluoroscopy, or x-rays. When guiding 52 the needle 36, the position of the needle 36 can be sensed by a variety of means such as by applying an electrical signal to the needle 36 to evoke a patient 24 response such as a motor or sensory response. Once the needle 36 is in position, the needle 36 can remain in the position to serve as a guide for the dilator 42, or in the alternative a guide wire 44 can be inserted through the needle 36. When the needle 36 is used as a guide for the dilator 42, the needle hub 45 typically must be removed before the dilator 42 can be guided over the needle 36. Alternatively, a guide wire 44 can be used as the guide for the dilator 42. The guide wire 44 can be a flexible guide wire, a stiff guide wire, or a stylet. Once the guide wire 44 is in position, the needle 36 can be removed, and the guide wire 44 can serve as a guide for the dilator 42.

The insertion path 33 is dilated 54 with a dilator 42 to a diameter sufficient for inserting a stimulation lead 30. The needle 36 is removed 56 from the insertion path 33, or alternatively the guide wire 44 is removed 56 from the insertion path 33. When removing 56 the needle 36 from the insertion path 33, care should be taken to avoid displacing the dilator 42. The stimulation lead 30 is inserted 58 to the desired location 35. Since the chronic stimulation lead 30 is being inserted 58 directly without the requirement for a separate test stimulation lead (not shown), such as a Medtronic Test Simulation Lead Model 3057, the chronic stimulation lead 30 can be placed without positioning repeatability variation. Also, there is a greater correlation between acute test stimulation and chronic therapy stimulation because the same lead 30 is performing both test stimulation and therapy stimulation. The desired location 35 can be any area of the sacrum 28 intended to achieve a therapeutic effect such as into the foremen 31. One way to verify the stimulation lead's 30 position is to apply an electrical signal to the stimulation lead 30 to evoke a patient 24 motor or sensory response. Other ways to verify the stimulation lead's 30 position include imaging techniques such as fluoroscopy and x-ray. When inserting 58 the implantable stimulation lead 30, the lead 30 is advanced through the dilator 42 to the desired location 35 for stimulation. The dilator 42 is removed 60 from the insertion path 33. When removing 60 the dilator 42 from the insertion path 33, care should be taken to avoid displacing the stimulation lead 30. Additionally, stimulation lead 30 position should be re-verified by one of the previously discussed techniques. Once the dilator 42 is removed, the clinician 22 may decide that the lead 30 does not need to be fixed because the patient's 24 physiology itself adequately stabilizes the lead 30. When the stimulation lead 30 is not separately fixed, patient 24 tissue disruption is minimized which provides for faster patient 24 recovery and potentially less stimulation lead 30 migration caused by disrupted tissue changes. If the clinician 22 does not wish to separately fix the stimulation lead 30, the first method embodiment 48 is completed. Optionally, the clinician 22 can separately fix the stimulation lead 30 by creating an incision 62, anchoring the lead 64, and closing the incision 66.

Figure 5A:
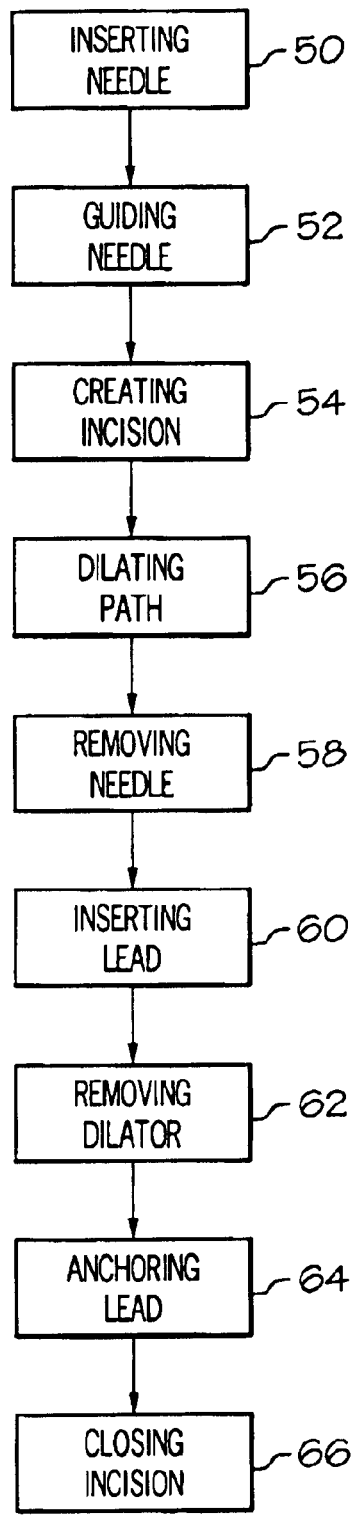
FIG. 5a shows a flowchart of a second minimally invasive method embodiment.
Figure 5B:
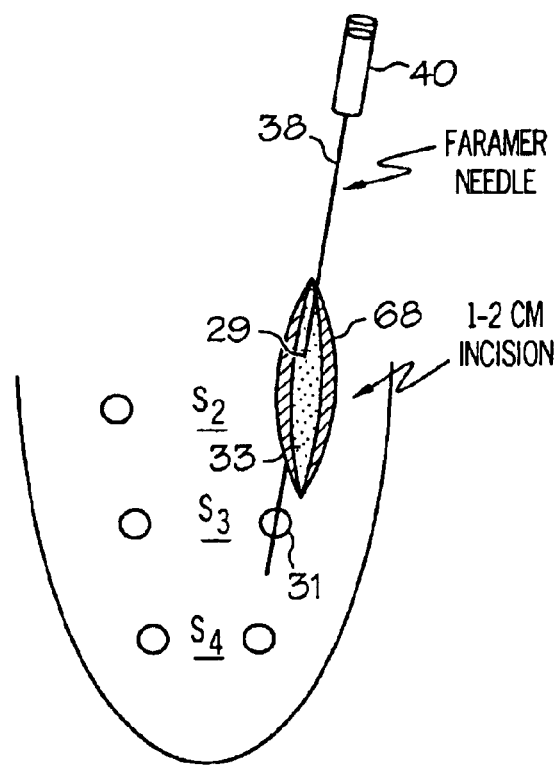
FIG. 5b shows a needle being inserted into a foramen embodiment.
Figure 5C:
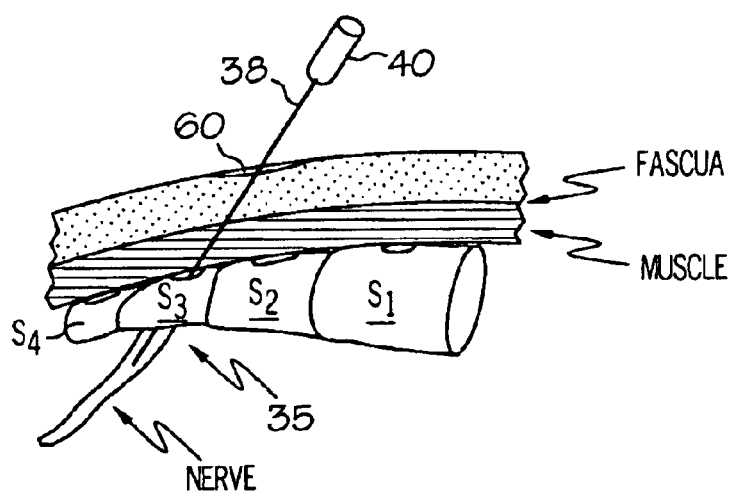
FIG. 5c shows a cross section view of FIG. 5b.
Figure 5D:
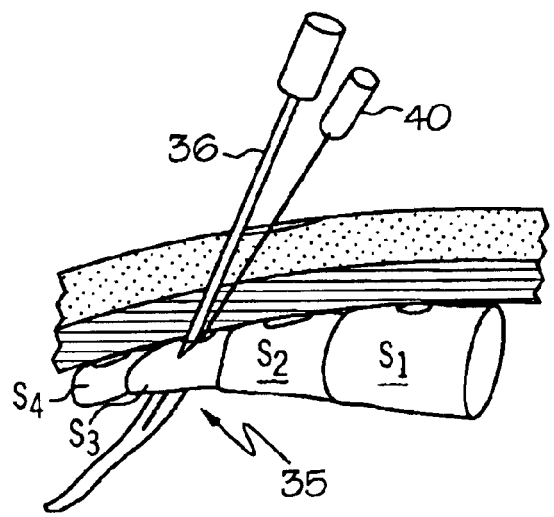
FIG. 5d shows the needle being used as a guide for a larger needle embodiment.
Figure 5E:
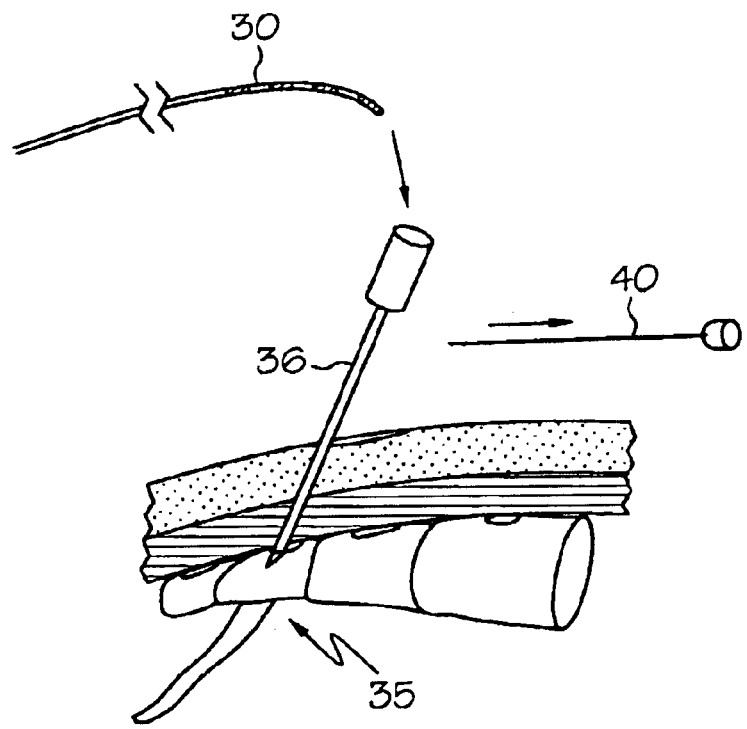
FIG. 5e shows removal of a stylet and insertion of a stimulation lead embodiment.
Figure 5F:
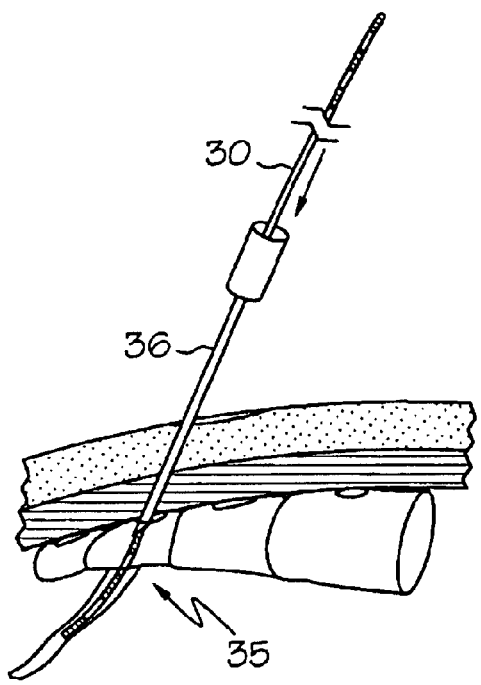
FIG. 5f shows another view of insertion of the stimulation lead embodiment.
Figure 5G:
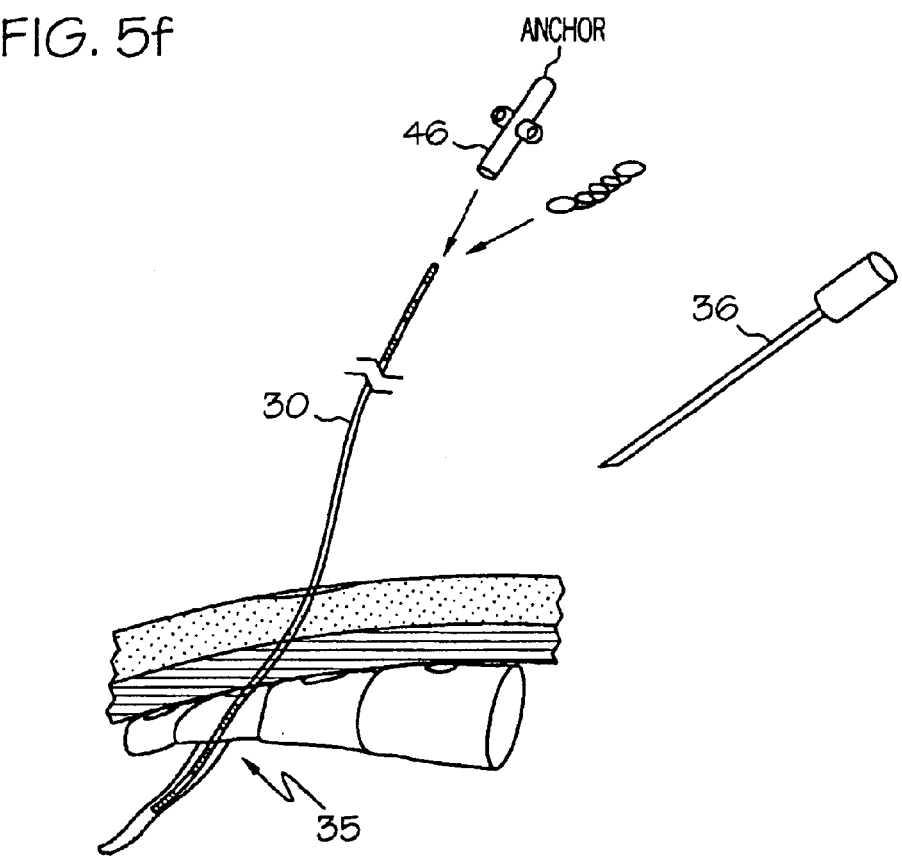
FIG. 5g shows removal of the needle and insertion of an anchor embodiment.
Figure 5H:
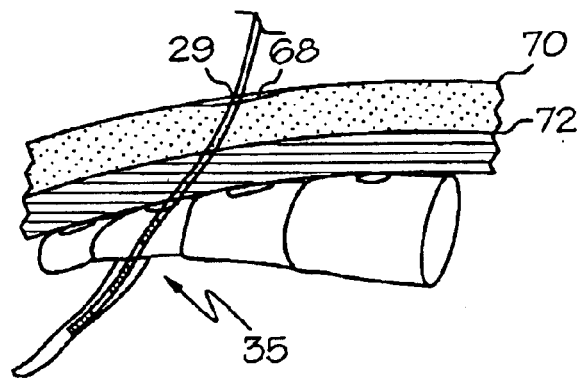
FIG. 5h shows fixation of the anchor embodiment.
Figure 5I:
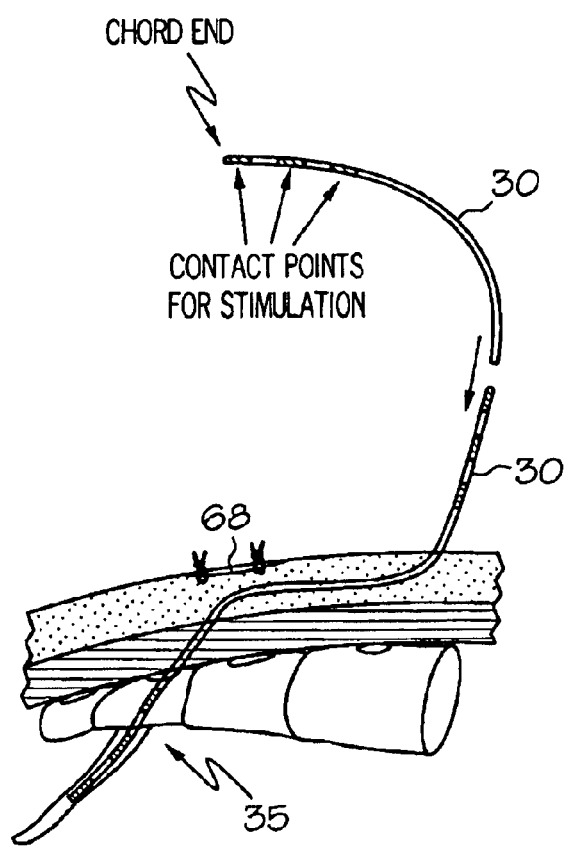
FIG. 5i shows another stimulation lead fixation embodiment.
Figure 5J:
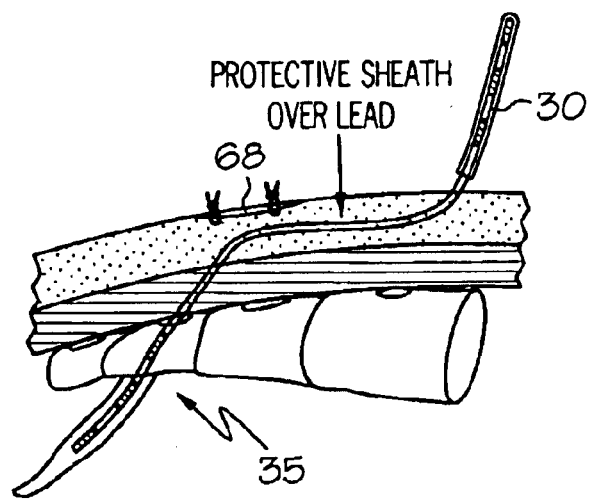
FIG. 5j shows another view of the stimulation lead fixation embodiment shown in the FIG. 5i embodiment.
Figure 5K:
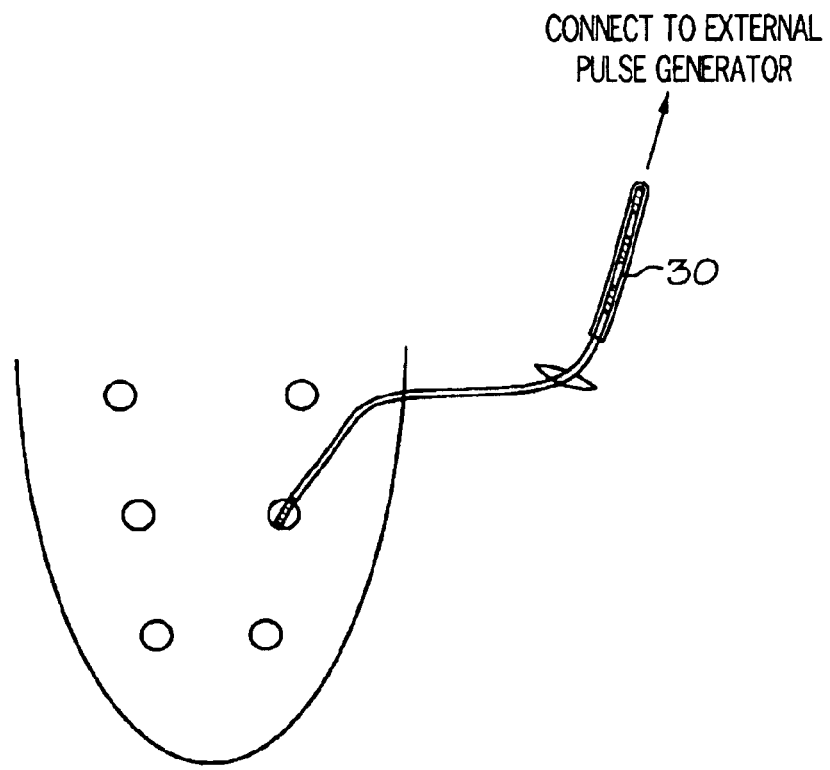
FIG. 5k shows an anchored stimulation lead that is tunneled for connection to a medical device.

FIG. 5h shows an embodiment for separately fixing the stimulation lead. To separately fix the stimulation lead 30, an incision 68 through the entry point 29 is created from an epidermis 70 to a fascia layer 72 such as the lumbosacral fascia layer. This incision 68 can also be created at a later point in the method embodiment 48 without adversely affecting the method. The stimulation lead 30 is anchored 64 to the fascia layer 72. When anchoring 64 the stimulation lead 64 care is again should be taken to avoid displacing the stimulation lead 30. Finally, the incision 68 created for the anchor is closed 66. Since the first method embodiment 48 disrupts less tissue than the prior art method, patient 24 tissue disruption is minimized which provides for faster patient recovery and potentially less stimulation lead 30 migration caused by disrupted tissue changes.

A portion of the first minimally invasive method embodiment 48 can also be used simply for stimulation lead 30 placement for acute test stimulation rather than implantation. For stimulation lead 30 placement, typically the same procedure is used as for implantation through removing the dilator 60 from the insertion path 33. Once the dilator 42 is removed, stimulation lead 30 placement is validated to ensure the stimulation lead 30 is in the desired location 35.

Second Minimally Invasive Method Embodiment

FIG. 5a shows a flowchart of a second minimally invasive implantation method embodiment 74, and FIGS. 5b–5k show various implementation element embodiments. The second minimally invasive method embodiment 74 is similar to the first minimally invasive method embodiment 48 with the exception that in the second method embodiment 74 includes an incision for anchoring that is created 62 after the needle has been guided 52 to a desired location 35 that is optional in the first method embodiment 48. By making the incision 62 earlier than optionally performed in the first minimally invasive method 48, the stimulation lead 30 can be more easily anchored 64 to a fascialu layer 72 such as the lumbosacral fascia layer closer to the stimulation lead 30 distal end.

A portion of the second minimally invasive method embodiment 74 can also be used simply for stimulation lead 30 placement for acute test stimulation rather than implantation. For stimulation lead 30 placement, typically the same procedure is used as for implantation through removing the dilator 60 from the insertion path 33. Once the dilator is removed 60, stimulation lead 30 placement is validated to ensure the stimulation lead 30 is in the desired location 35.

Third Minimally Invasive Method Embodiment

Figure 6A:
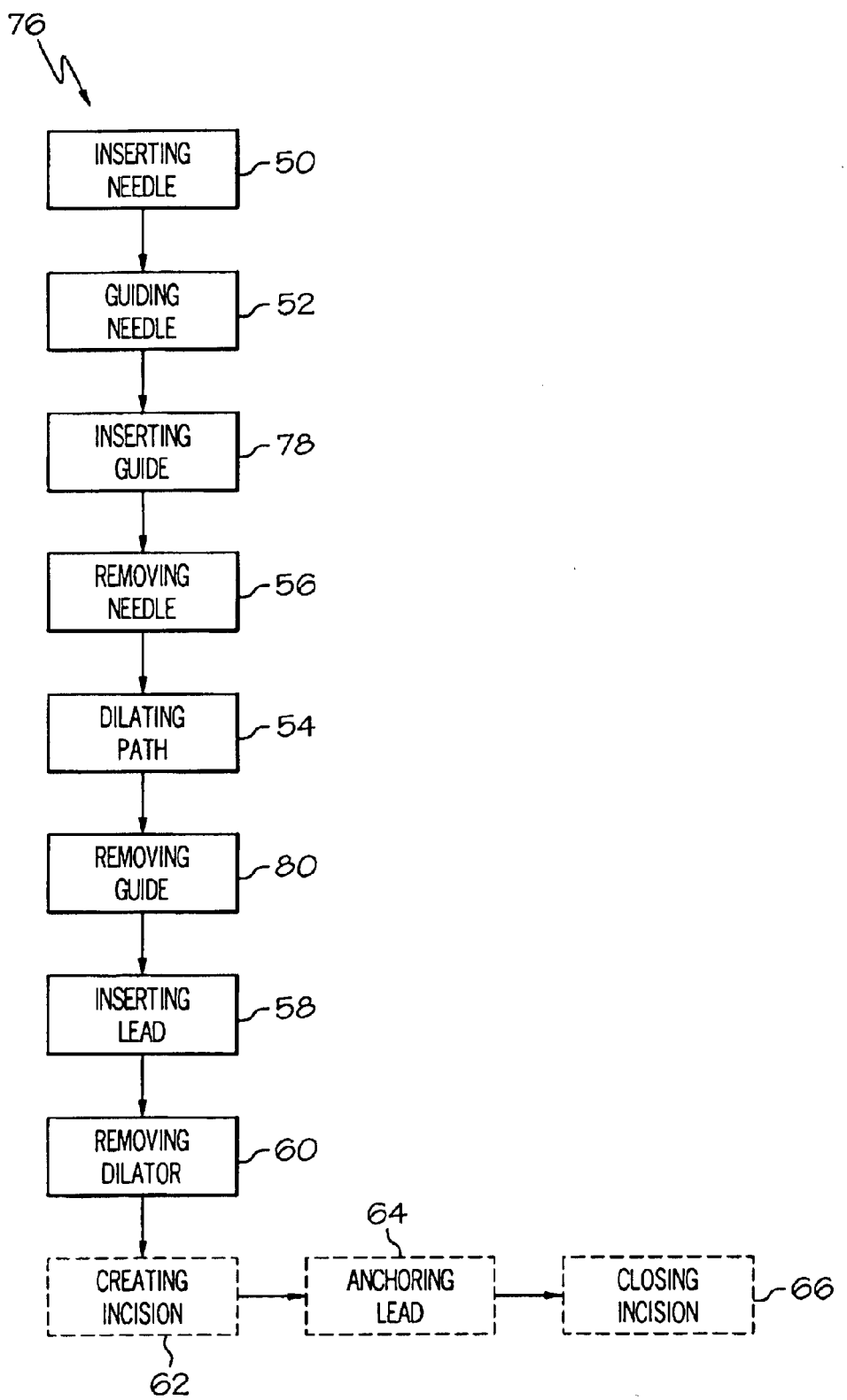
FIG. 6a shows a flowchart of a third minimally invasive method embodiment.
Figure 6E:
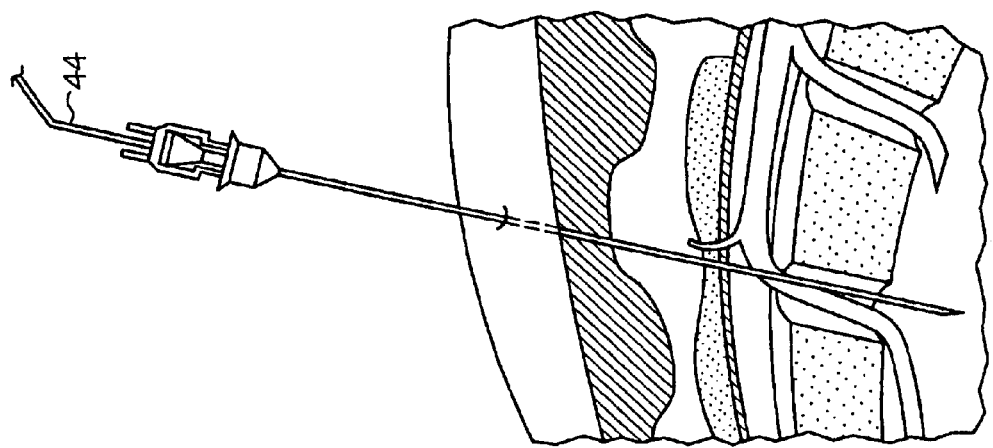
FIG. 6e shows an anatomical drawing of the guide wire inserted as shown in the FIG. 6d embodiment.
Figure 6D:
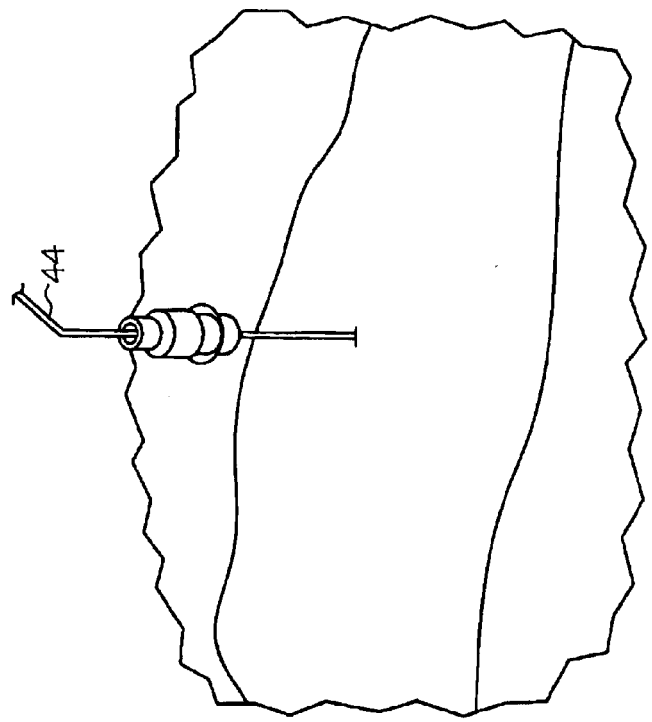
FIG. 6d shows a patient having a guide wire inserted through the needle.
Figure 6G:
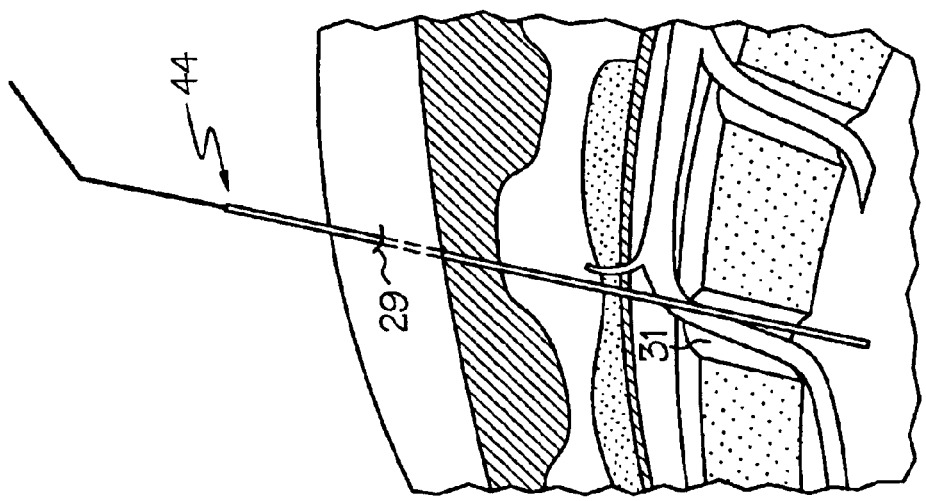
FIG. 6g shows an anatomical drawing of the dilator placed over the guide wire as shown in the FIG. 6f embodiment.
Figure 6F:
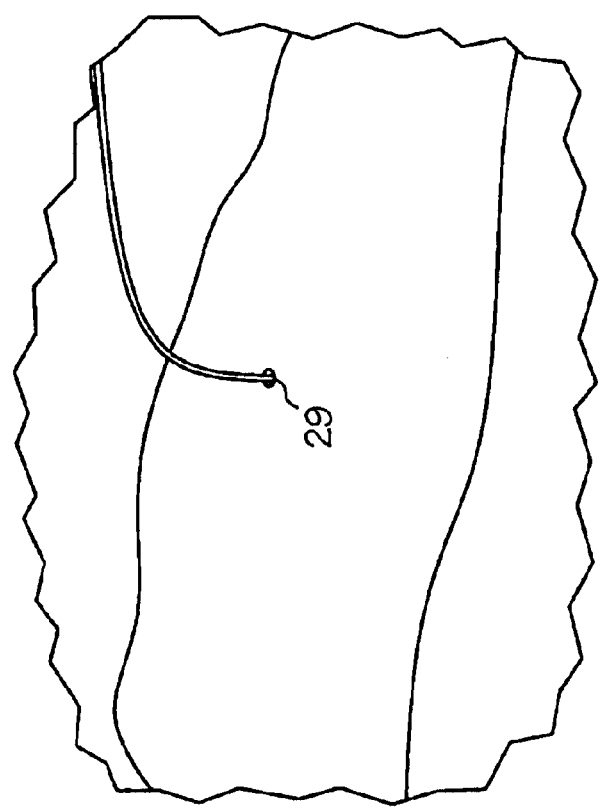
FIG. 6f shows a patient having a dilator placed over the guide wire embodiment.
Figure 6I:
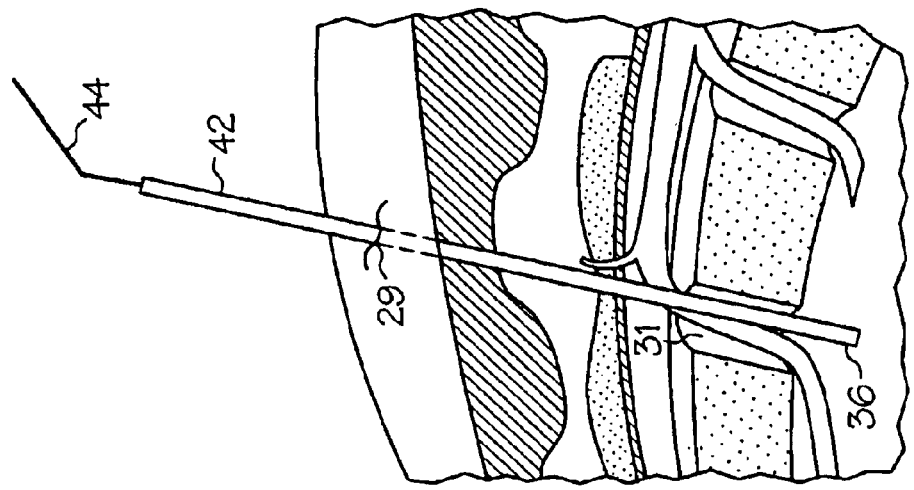
FIG. 6i shows an anatomical drawing of the dilator inserted into the sacrum as shown in the FIG. 6h embodiment.
Figure 6H:
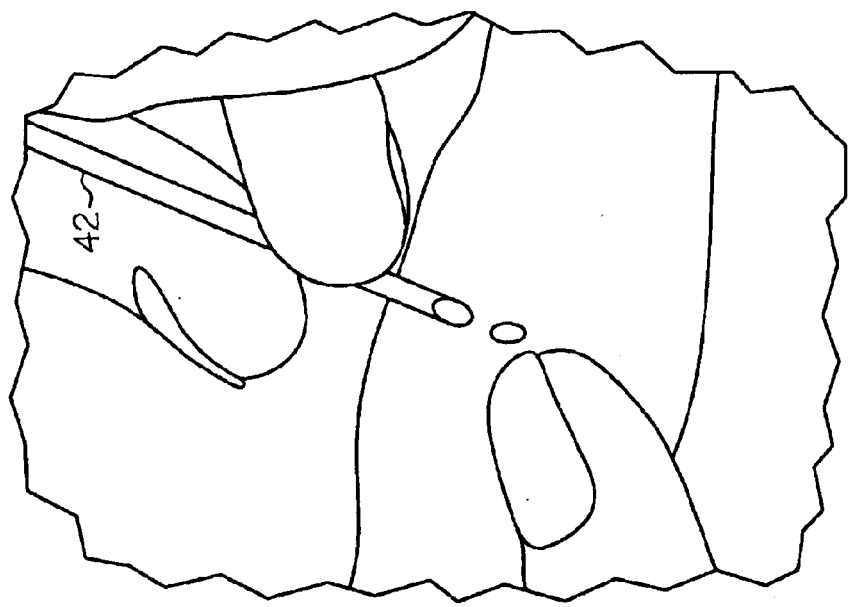
FIG. 6h shows a patient having the dilator inserted into the sacrum embodiment.
Figure 6K:
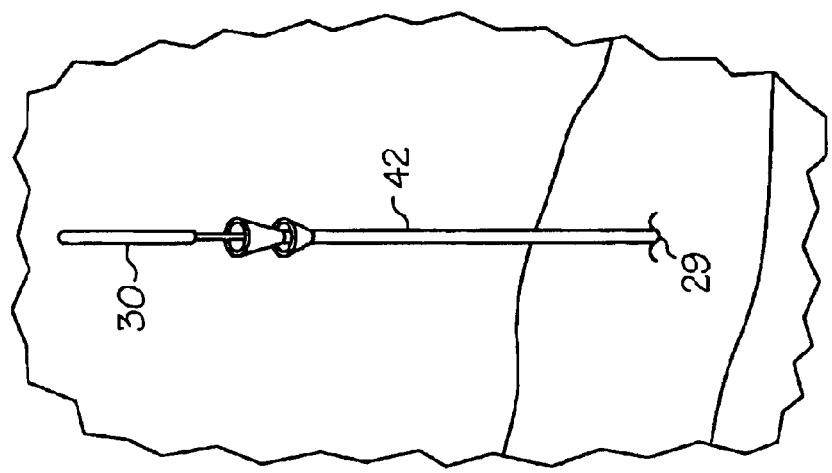
FIG. 6k shows inserting the stimulation lead into the dilator embodiment.
Figure 6J:
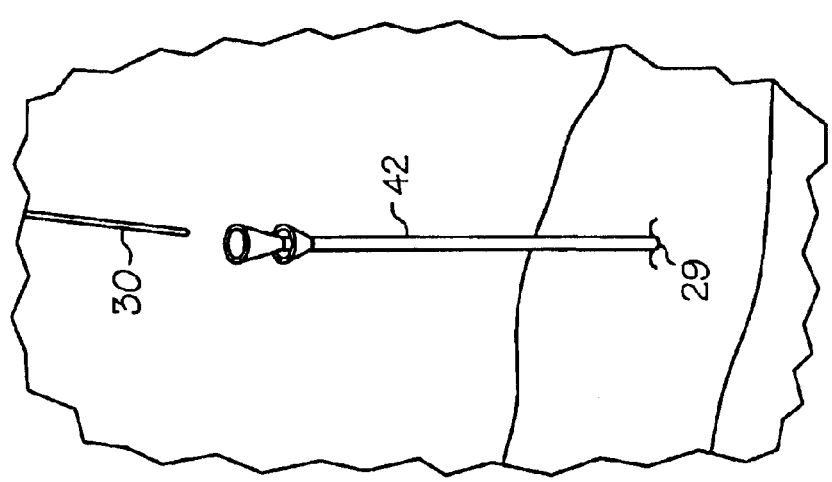
FIG. 6j shows preparation for inserting the stimulation lead into the dilator embodiment.
Figure 61:
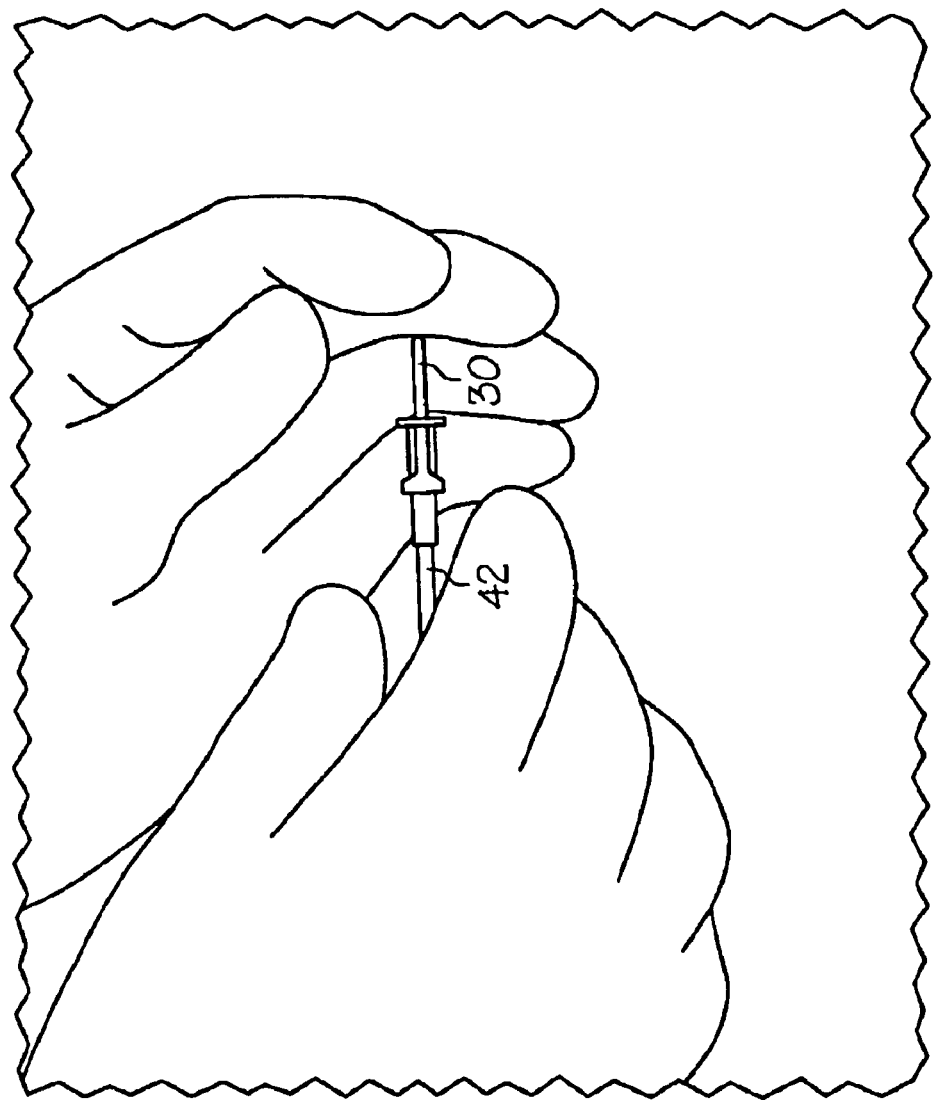
Figure 6O:
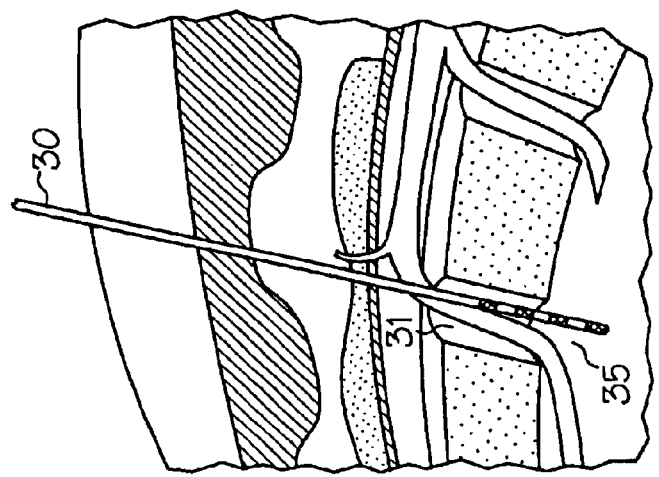
FIG. 6o shows an anatomical cross-section drawing of marking the stimulation lead embodiment.
Figure 6M:
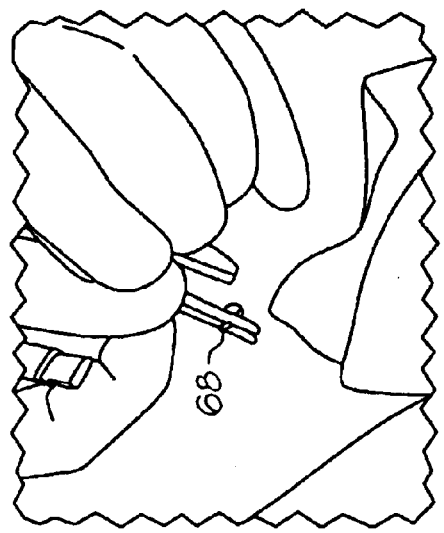
FIG. 6m shows creating an incision at the stimulation lead insertion site embodiment.
Figure 6N:
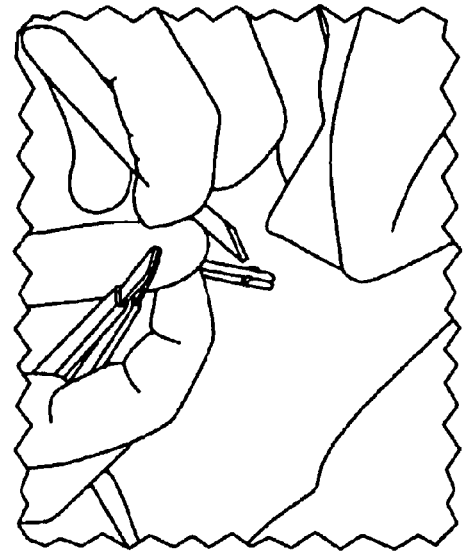
FIG. 6n shows marking the stimulation lead embodiment.
Figure 6Q:
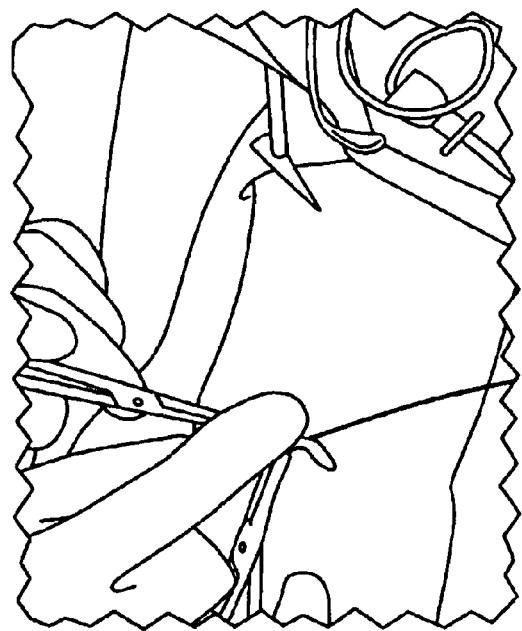
FIG. 6q shows tunneling the stimulation lead embodiment.
Figure 6P:
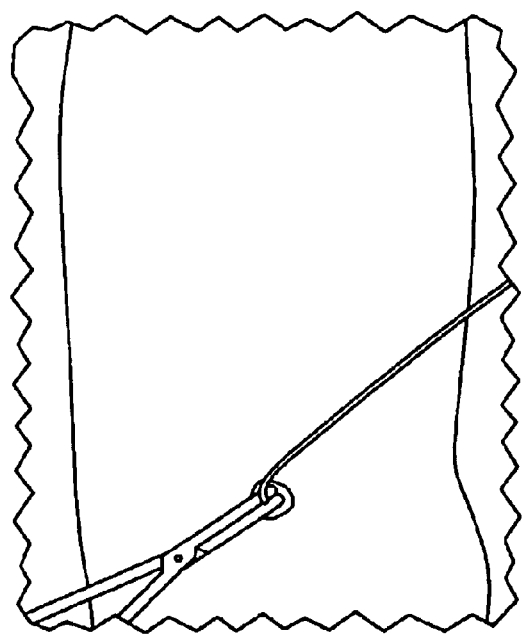
FIG. 6p shows applying a lead anchor to the stimulation lead embodiment.
Figure 6S:
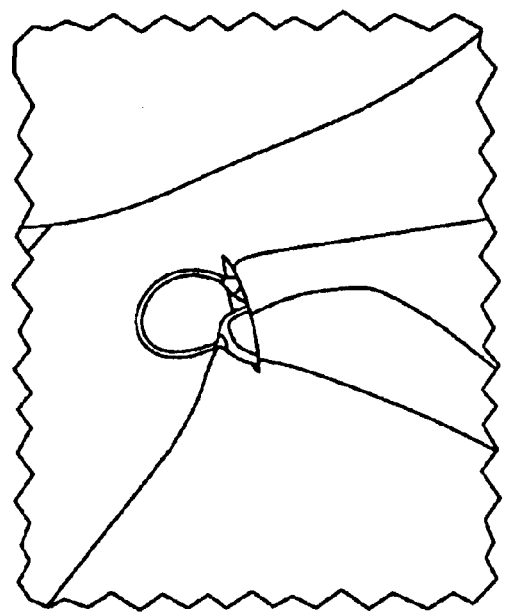
FIG. 6s shows fixation of the lead anchor to fascia of the patient embodiment.
Figure 6R:
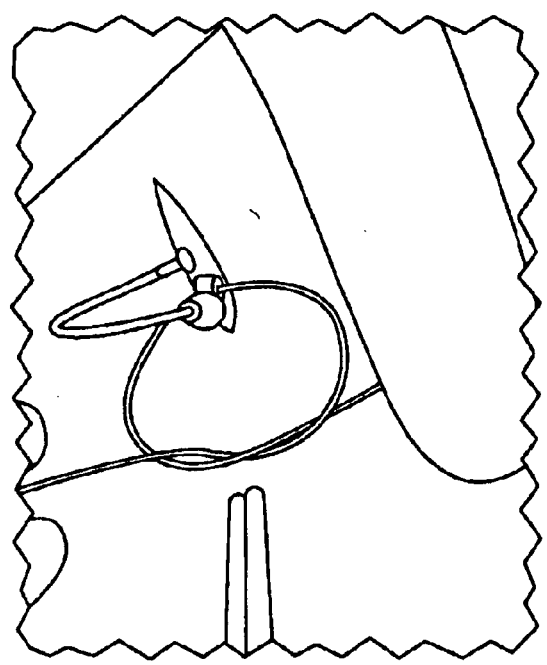
FIG. 6r shows fixation of the lead anchor to the lead body embodiment.

FIG. 6a shows a flowchart of a third minimally invasive implantation method embodiment 76, and FIGS. 6b–6o show various implementation element embodiments. The third minimally invasive method embodiment 76 is similar to the first minimally invasive method embodiment 48 with the exception that a guide wire 44, stylet, or long needle is inserted 78 to guide the dilator 42 and the guide wire 44 is removed 80 after dilation has been completed. More specifically, after the needle 36 has been guided 52 into the foramen along an insertion path 33 to a desired location 35, a guide wire 44 is inserted into the needle 36 to the desired location 35. Once the guide wire 44 is in place, the needle 36 is removed 56 while retaining the guide wire 44 at the desired location 35. The dilator 42 is placed over the guide wire 44 along the insertion path 33 to dilate 54 the insertion path 33 to a diameter sufficient for inserting 58 a stimulation lead 30. Once the dilator 42 is in place, the guide wire 44 is removed 80 from the dilator 42. After the stimulation lead 30 is in the desired location 35, the dilator 42 is removed 60. With the third minimally invasive method 76, once the dilator 42 is removed 60, the additional steps of creating an incision 62, anchoring the lead 64, and closing the incision 66 are optional. Once the dilator 42 is removed 60, the clinician 22 may decide that the stimulation lead 30 does not need to be fixed because the patient's 24 physiology itself adequately stabilizes the stimulation lead 30. If the clinician 22 determines the patient 24 requires the stimulation lead 30 fixation, then the clinician 22 would perform the elements of creating an incision 62, anchoring the lead 64, and closing the incision 66 as discussed previously.

A portion of the third minimally invasive method embodiment 76 can also be used simply for stimulation lead 30 placement for acute test stimulation rather than implantation. For stimulation lead 30 placement, typically the same procedure is used as for implantation through removing 60 the dilator 42 from the insertion path. Once the dilator 42 is removed 60, stimulation lead 30 placement is validated to ensure the stimulation lead 30 is in the desired location 35.

Fourth Minimally Invasive Method Embodiment

Figure 7A:
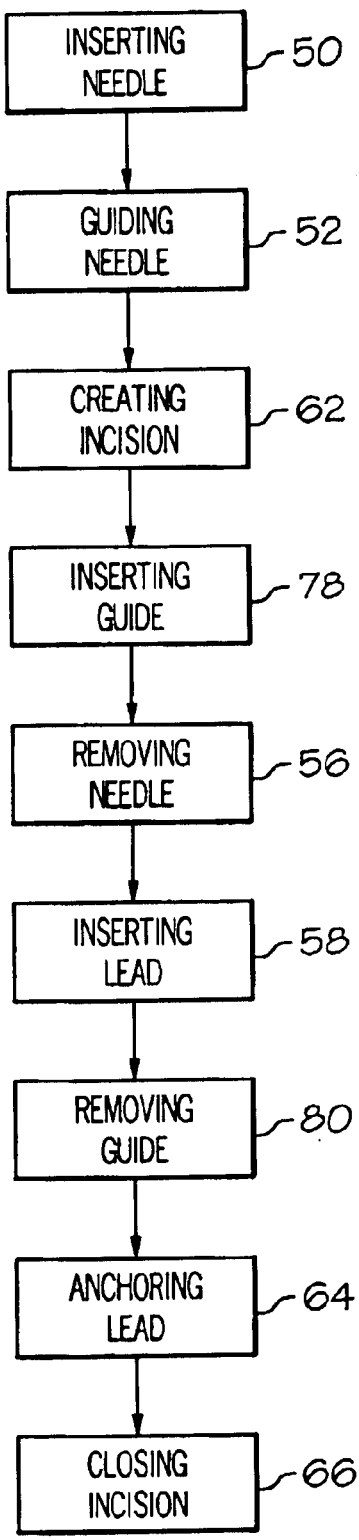
FIG. 7a shows a flowchart of a fourth minimally invasive embodiment.
Figure 7B:
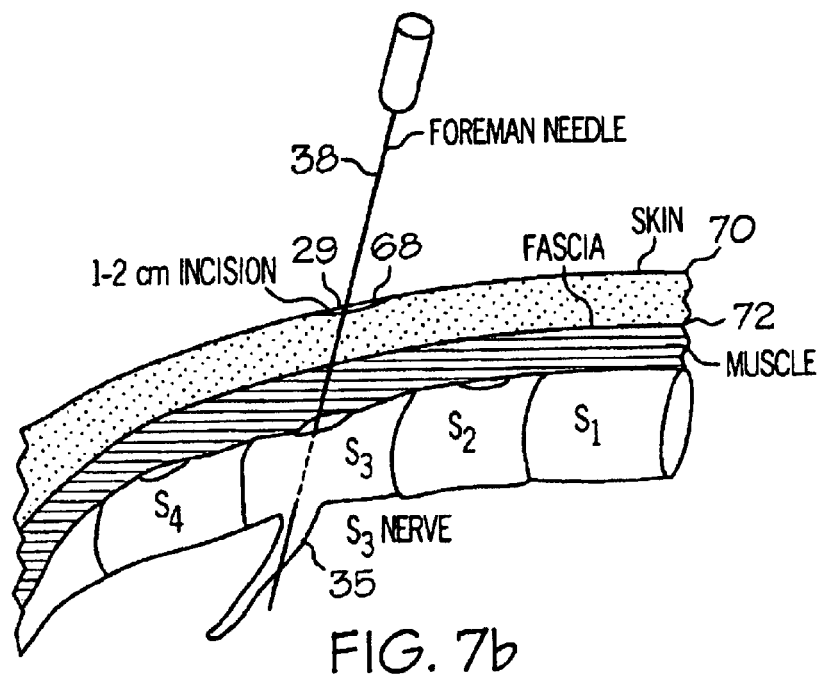
FIG. 7b shows an anatomical cross-section of creating an incision and inserting the needle embodiment.
Figure 7C:
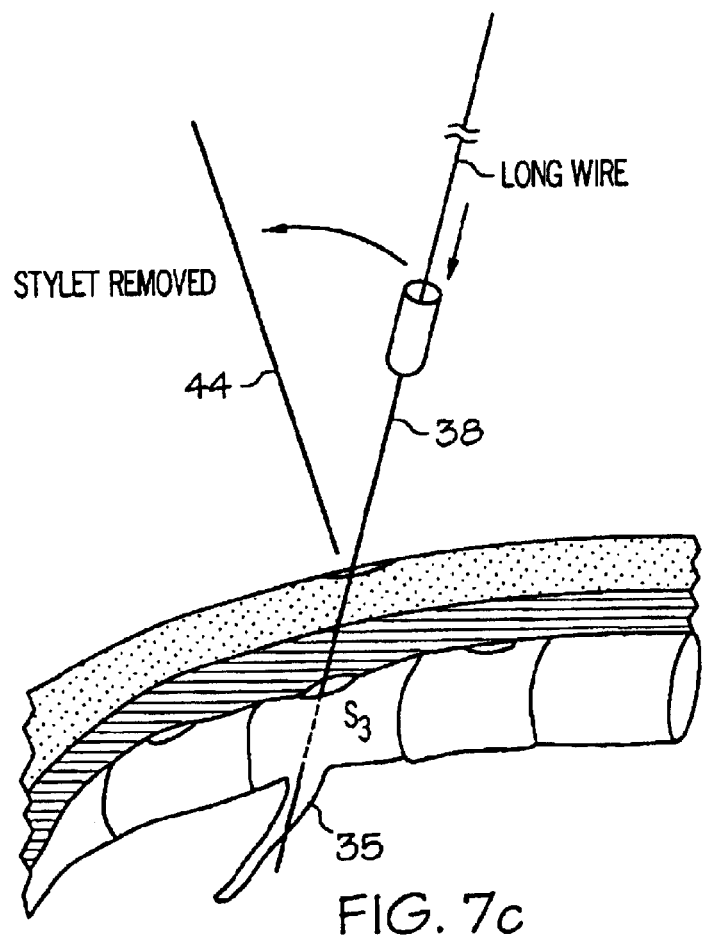
FIG. 7c shows an anatomical cross-section of insertion of the guide embodiment.
Figure 7D:
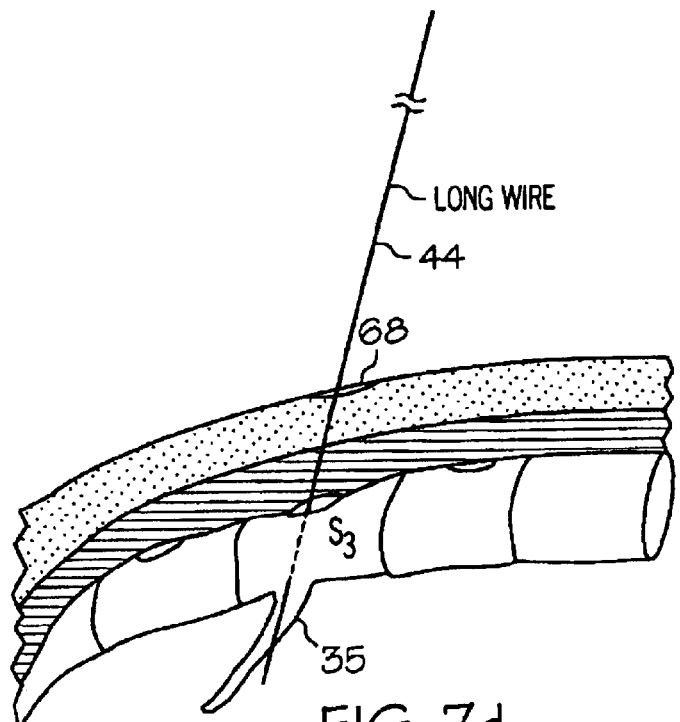
FIG. 7d shows an anatomical cross-section of the guide in place after the needle has been removed embodiment.
Figure 7E:
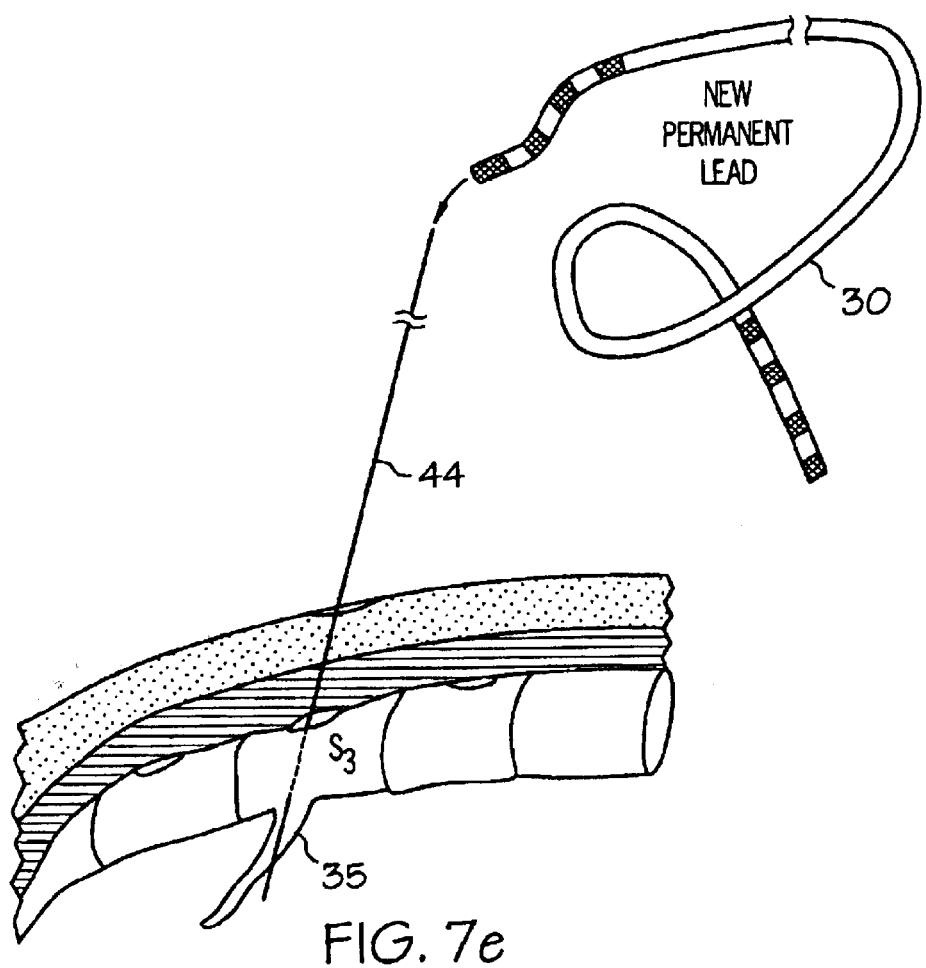
FIG. 7e shows an anatomical cross-section of placement of the stimulation lead over the guide embodiment.
Figure 7F:
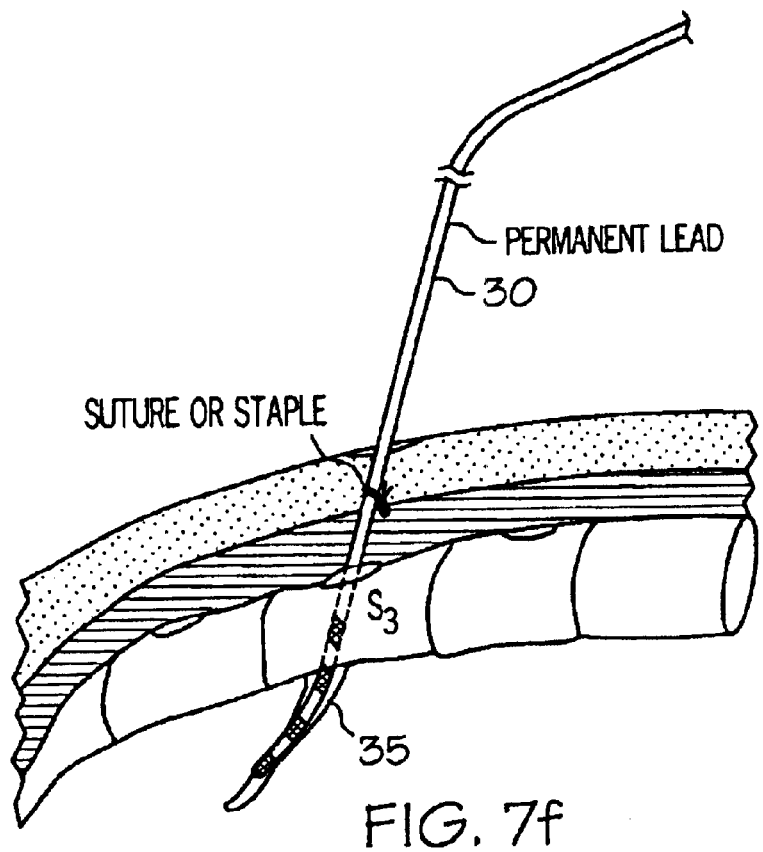
FIG. 7f shows an anatomical cross-section of fixing the stimulation lead to a patient's fascia and removal of the guide embodiment.
Figure 7G:
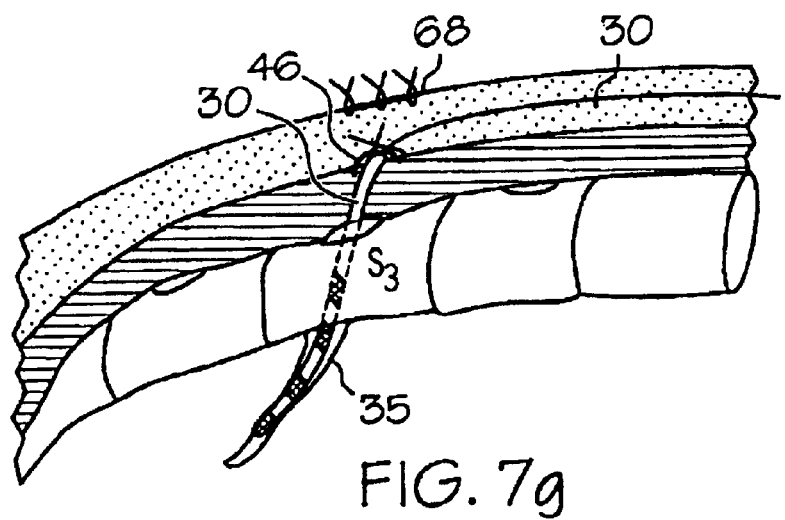
FIG. 7g shows an anatomical cross-section of closing the incision and tunneling the stimulation lead embodiment.

FIG. 7a shows a flowchart of a fourth minimally invasive implantation method embodiment 82, and FIGS. 7b–7g show various implementation element embodiments. The fourth minimally invasive method embodiment 82 is similar to the second minimally invasive method embodiment 74 with the exception that a guide wire 44 or stylet is inserted 78 to guide the stimulation lead 30 and the stimulation lead 30 functions as the dilator 42, so a separate dilator 42 is not used. More specifically, after the incision 68 is created 62, a guide wire 44 is inserted 78 into the needle. Once the guide wire 44 is in the desired location 35, the needle 36 is removed 56 from the insertion path 33. In one embodiment, the stimulation lead 30 is configured with a centrally located stylet lumen and a pointed tip, so the stimulation lead 30 can serve as the dilator 42. The stimulation lead 30 stylet lumen is inserted 58 over the guide wire 44 and the stimulation lead 30 is advanced to the desired location 35. After the stimulation lead 30 is in the desired location 35, the guide wire 44 is removed 80 from the stimulation lead 30. Then the stimulation lead 30 is anchored 64 and the incision 68 is closed 66 similar to the second minimally invasive method embodiment 74.

A portion of the fourth minimally invasive method embodiment 82 can also be used simply for stimulation lead 30 placement for acute test stimulation rather than implantation. For stimulation lead 30 placement, typically the same procedure is used as for implantation through removing 80 the guide wire 44 from the stimulation lead 30. Once the guide wire 44 is removed, stimulation lead 30 placement is validated to ensure the stimulation lead 30 is in the desired location 35.

Fifth and Sixth Minimally Invasive Method Embodiments

Figure 8A:
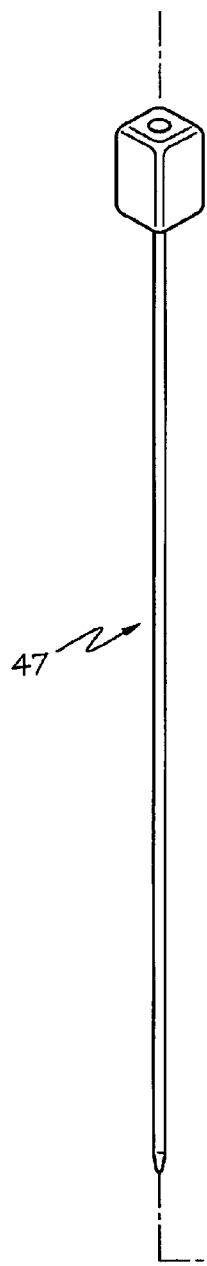
FIGS. 8a–8c shows a variation of the dilator of FIG. 3e usable in any of the procedures described herein comprising a dilator formed of the assembly of a dilator body and a dilator sheath.
Figure 8B:
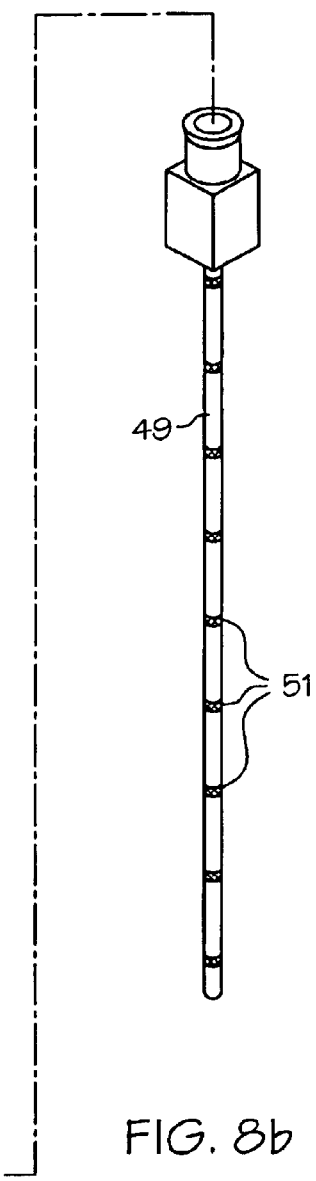
Figure 8C:
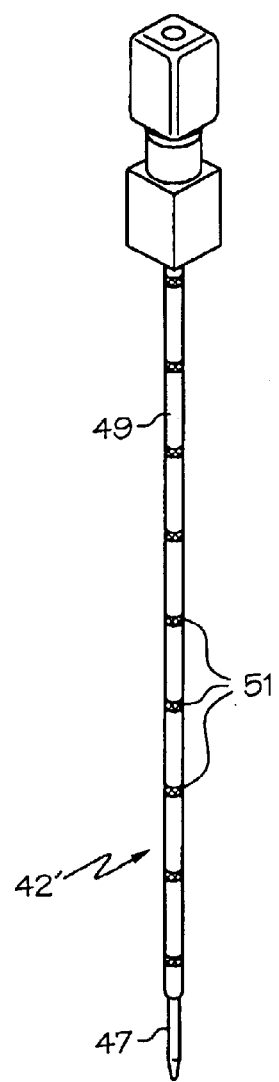

The above described instrument kits used in the first through fourth embodiments are modified by substitution of a dilator 42' formed of the assembly of a dilator body 47 and a dilator sheath 49 as shown in FIGS. 8a–8c. The dilator body 47 is preferably conductive, and the dilator sheath 49 is preferably non-conductive but may bear radiopaque and visually observable depth marks 51 along its length to facilitate radiographic imaging when it is extended into the patient's body. The depth markings or marks 51 can be one centimeter or one-half centimeter bands or numerals or other indicia that indicate the depth of insertion to clinician from the exposed marking. The most distal mark is spaced from the distal tip of dilator sheath 49 to indicate a predetermined depth of the distal tip of the dilator body 47 protruding distally during insertion as shown in FIG. 8c.

Thus, when assembled as shown in FIG. 8c, the dilator body distal end extends out of the dilator sheath distal end and is electrically exposed. Electrical stimulation of the sacral nerve to test placement can take place through the dilator body 47 while the dilator sheath 49 is in place The dilator body 47 has a dilator body diameter, a dilator body length extending between a dilator proximal end and a dilator distal end, and a dilator body lumen extending from the dilator proximal end to the dilator distal end. The dilator sheath has a dilator sheath diameter, a dilator sheath length extending between a dilator sheath proximal end and a dilator sheath distal end. A dilator sheath lumen extends from the dilator sheath proximal end to the dilator sheath distal end, the dilator sheath lumen having a dilator sheath lumen diameter sized in operative relation to the dilator body diameter to selectively receive the dilator body therein to assemble the dilator body and dilator sheath as the dilator as shown in FIG. 8c. The dilator sheath lumen is also sized in operative relation to the diameter of the neurostimulation lead body so that the neurostimulation lead can be advanced through the dilator sheath.

Figure 8D:
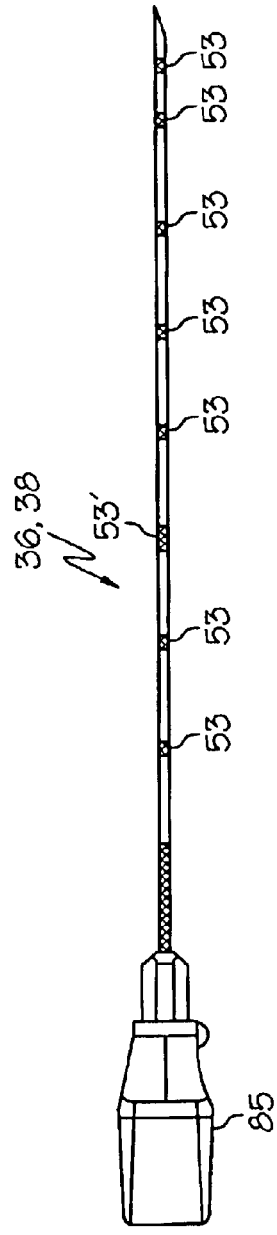
FIG. 8d shows a needle or foramen needle having a hub and depth marks along the needle body.
Figure 8E:
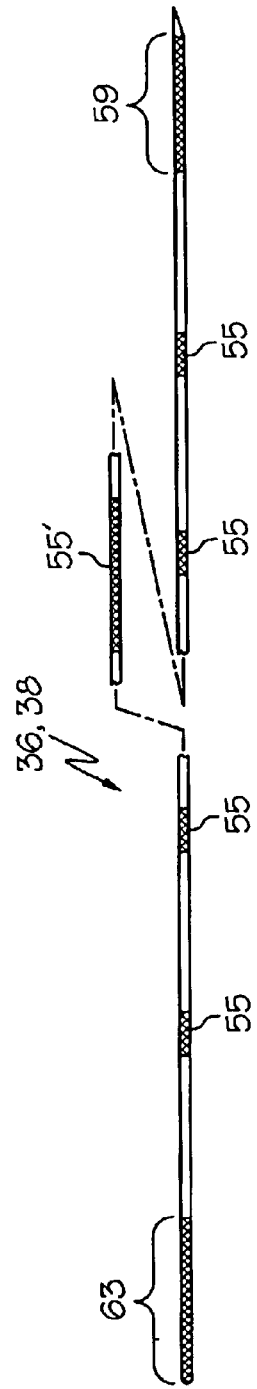
FIG. 8e shows a needle or foramen needle without a hub and with depth marks along the needle body.
Figure 8F:
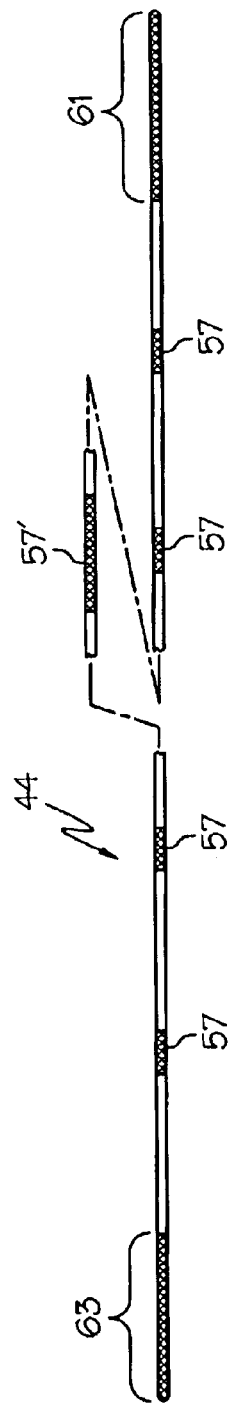
FIG. 8f shows a guide wire having depth marks along its length.

The needle 36 or foramen needle 38 is also shown in FIG. 8d with a hub 45 and with depth marks 53 in FIG. 8e and without a hub and with depth marks 55. The guide wire 44 is also shown in FIG. 8f marked with further depth marks 57. In addition, the body of the neurostimulation lead 30 is marked with depth marks. The depth mark 53' is widened or otherwise made distinguishable to indicat a particular depth, e.g., 5 cm, to assist the clinician in keeping track of the marks 53.

These depth marks 53, 55, 57 are correlated to one another and to the depth marks 51 so that the depth of insertion from the skin of each instrument is ascertainable from the proximal exposed marks. These marks 53, 55, 57 can be observed to maintain the depth while manipulating the instruments to assure that the clinician extends each instrument to the same depth. Similarly, the depth marks on the neurostimulation lead 30 are correlated to the length of the dilator 42 or the dilator sheath 49 to properly locate a neurostimulation lead electrode in operative relation to the sacral nerve. and lead electrode(s)

For example, one of the depth marks of each set can be widened or otherwise made distinguishable from the others so that the clinician can tell when the distal end or distal electrode(s) of the instrument or lead introduced through the lumen or over an instrument already placed to the site is properly positioned at the site. In FIG. 8f, a mark 57' is placed along the guide wire body at a distance from the distal end that, when exposed from the needle hub 45 or a dilator hub indicates that the distal end of the guide wire 44 is positioned at the distal end of the needle 36, 38 or dilator 42'. Conversely, a dilator 42, 42' or lead 30 is inserted over the guide wire 44 until the mark 57' is exposed showing that the distal end of the dilator 42, 42' or lead 30 is properly advanced over the guide wire 44 to the desired site. Similarly, in a variation where a dilator 42 or 42' is inserted over the needle 36, 38 depicted in FIG. 8e, a mark 55' placed along the needle body at a distance from the distal end is exposed from the dilator hub that signifies that the dilator distal tip is at the desired site.

The needle 36, 38, dilator 42' and guide wire 44 are all preferably formed of a conductive material insulated along the exposed lengths thereof but exposed at or along the proximal and distal ends thereof so as to be capable of being used to conduct test stimulation to the sacral nerve to assess the efficacy of stimulation prior to implantation of the neurostimulation lead and to establish the depth of positioning of the neurostimulation lead electrode. For example, an exposed distal electrode 59 and an exposed proximal connector element 63 is depicted on needle 36, 38 in FIG. 8e, and an exposed distal electrode 61 and an exposed proximal connector element 65 is depicted on guide wire 44 in FIG. 8f. The dilator body lumen has a dilator body lumen diameter sized in operative relation to the diameter of guide wire 44 or needle 36 or 38 so that the assembled dilator can be advanced over the guide wire 44 in accordance with the method depicted in FIG. 9a or over the needle 36 or 38 in accordance with the method depicted in FIG. 10.

Figure 9B:
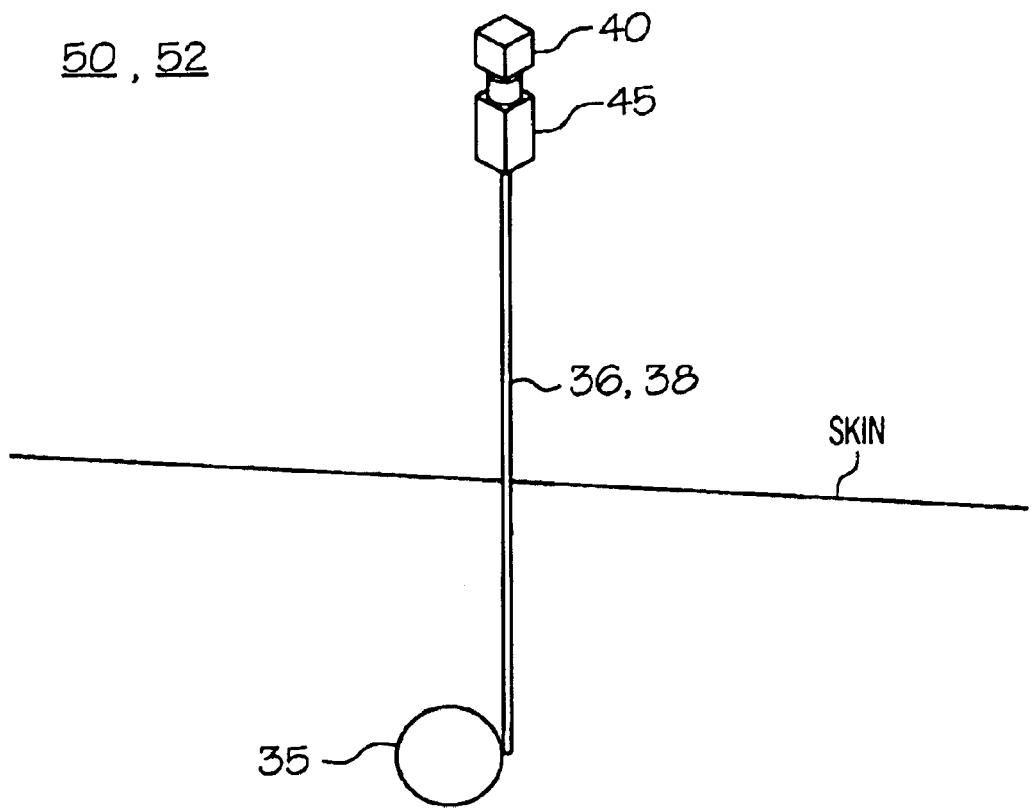
FIG. 9b shows inserting and guiding a needle, e.g., a foramen needle, comprising a hollow needle body and an obturator within the needle body lumen to the sacral nerve site.

FIG. 9a shows a flowchart of a fifth minimally invasive method embodiment employing the dilator 42' of FIGS. 8a–8c along with the needle 36 of FIGS. 3a and 8 or foramen needle 38 of FIG. 3d and a guide wire 44. Many of the steps of FIG. 9a are common to the steps of FIGS. 4, 5a, 6a, and 7a, and commonly enumerated. FIG. 9b shows inserting and guiding a needle 36, e.g., a foramen needle 36, comprising a hollow needle body and a stylet or obdurator 40 within the needle body lumen, to the sacral nerve site in accordance with steps 50 and 52. The needle 36, 38 is electrically insulated along its length except along the distal tip and preferably has depth marks spaced along the needle shaft or body as described above that the clinician observes while advancing the needle distal tip to the desired location 35 within or through the foramen and adjoining the sacral nerve. The proximal end of the obdurator 40 can be coupled to a neurostimulator to deliver neurostimulation to test the stimulation efficacy at the location 35.

Figure 9C:
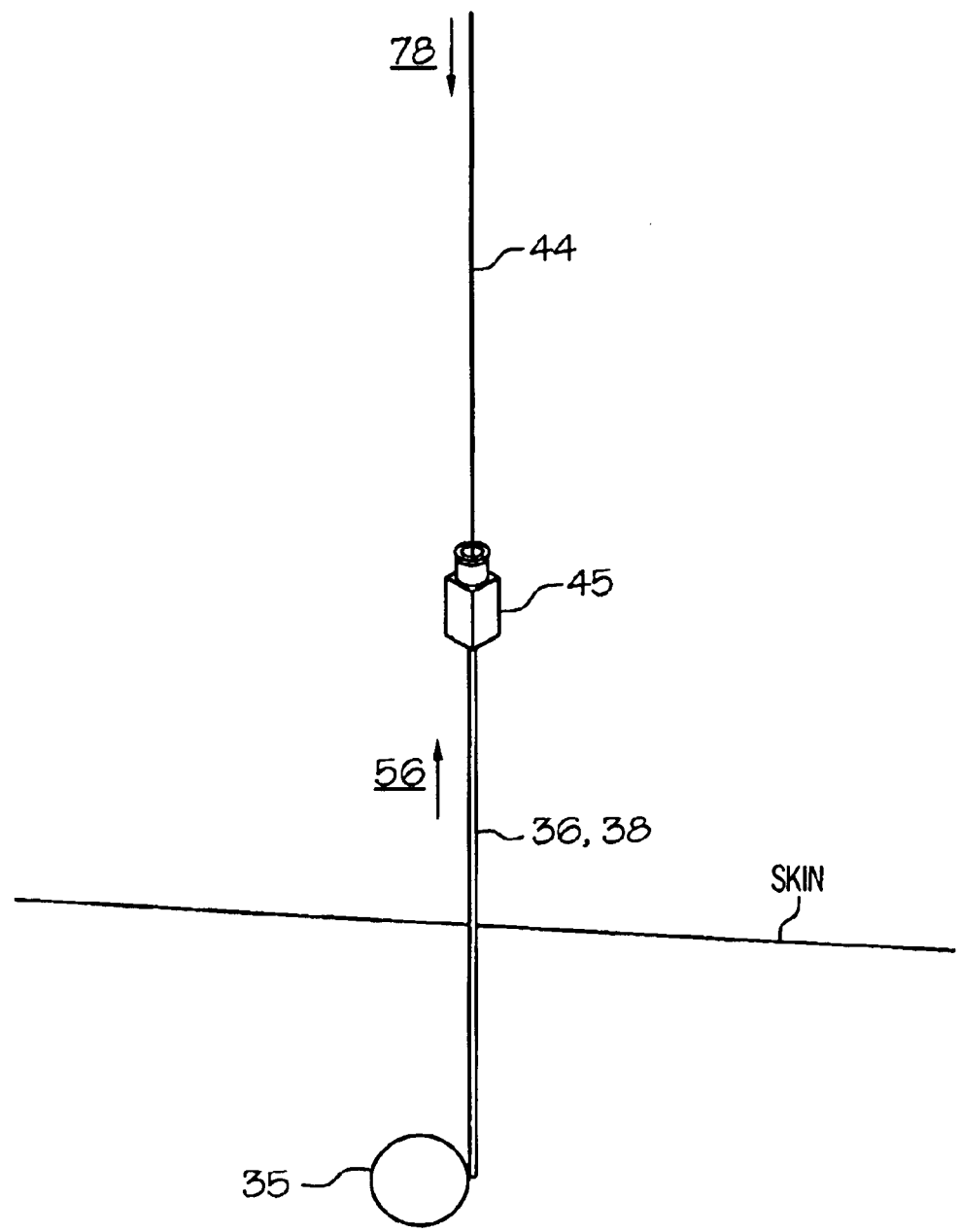
FIG. 9c shows inserting and advancing a guide wire through the needle body lumen after electrical testing and removal of the obturator from the needle body lumen.

FIG. 9c shows inserting and advancing a guide wire 44 through the needle body lumen after electrical testing and removal of the obdurator 40 from the needle body lumen in accordance with step 78. The guide wire 44 is advanced until the guide wire marking 57' abuts the needle hub 45 or needle proximal end if a needle 36, 38 of the type depicted in FIG. 8e is employed. FIG. 9c also shows withdrawal of the needle 36, 38 over the guide wire 44 in accordance with step 56, leaving the guide wire 44 in place extending from its distal end at the desired location 35 and its proximal end projecting from the patient's skin.

Figure 9D:
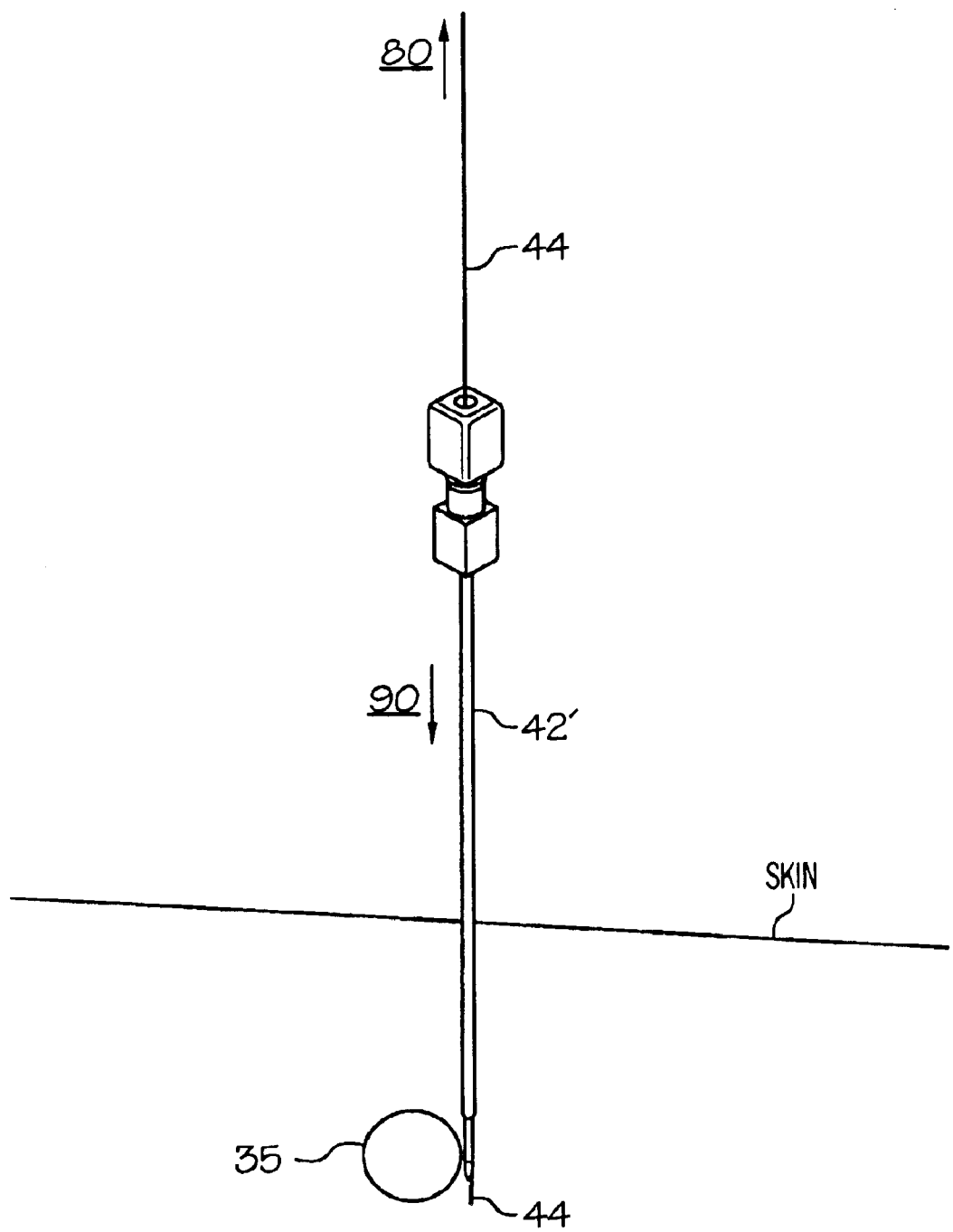
FIG. 9d shows advancing the dilator of FIG. 8c over the guide wire to locate the distal end of the guide wire at the sacral nerve and then withdrawing the guide wire from the dilator body lumen.

Preferably, the guide wire 44 is stiff and straight and is long enough so that the dilator 42' can be inserted over the guide wire 44 outside of the patient's skin. The proximal end of the guide wire 44 can then be grasped as the dilator 42' is advanced over and past it. FIG. 9d shows advancing the dilator 42' of FIG. 8c over the guide wire 44 to locate the distal end of the guide wire 44 at the desired location 35 adjoining the sacral nerve in accordance with step 90 and then withdrawing the guide wire 44 from the dilator body lumen in accordance with step 80. Again, the dilator 42' is advanced distally over the guide wire 44 until the mark 57' is exposed, which indicates that the dilator body distal end is at the desired location 35.

Figure 9E:
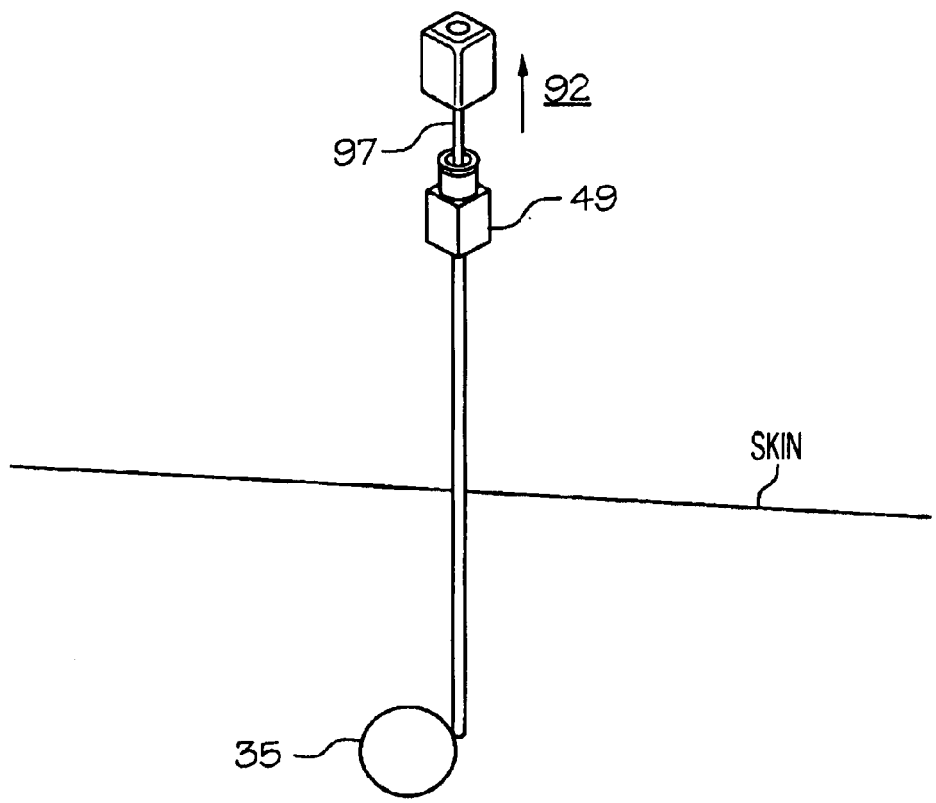
FIG. 9e shows withdrawal of the dilator body from the dilator sheath.

FIG. 9e shows withdrawal of the dilator body 47 from the dilator sheath 49 in accordance with step 92. The depth marking on the dilator sheath surface exposed at the skin incision is observed to ensure that the dilator sheath 49 is not inadvertently advanced or withdrawn as the dilator body is withdrawn.

Figure 9F:
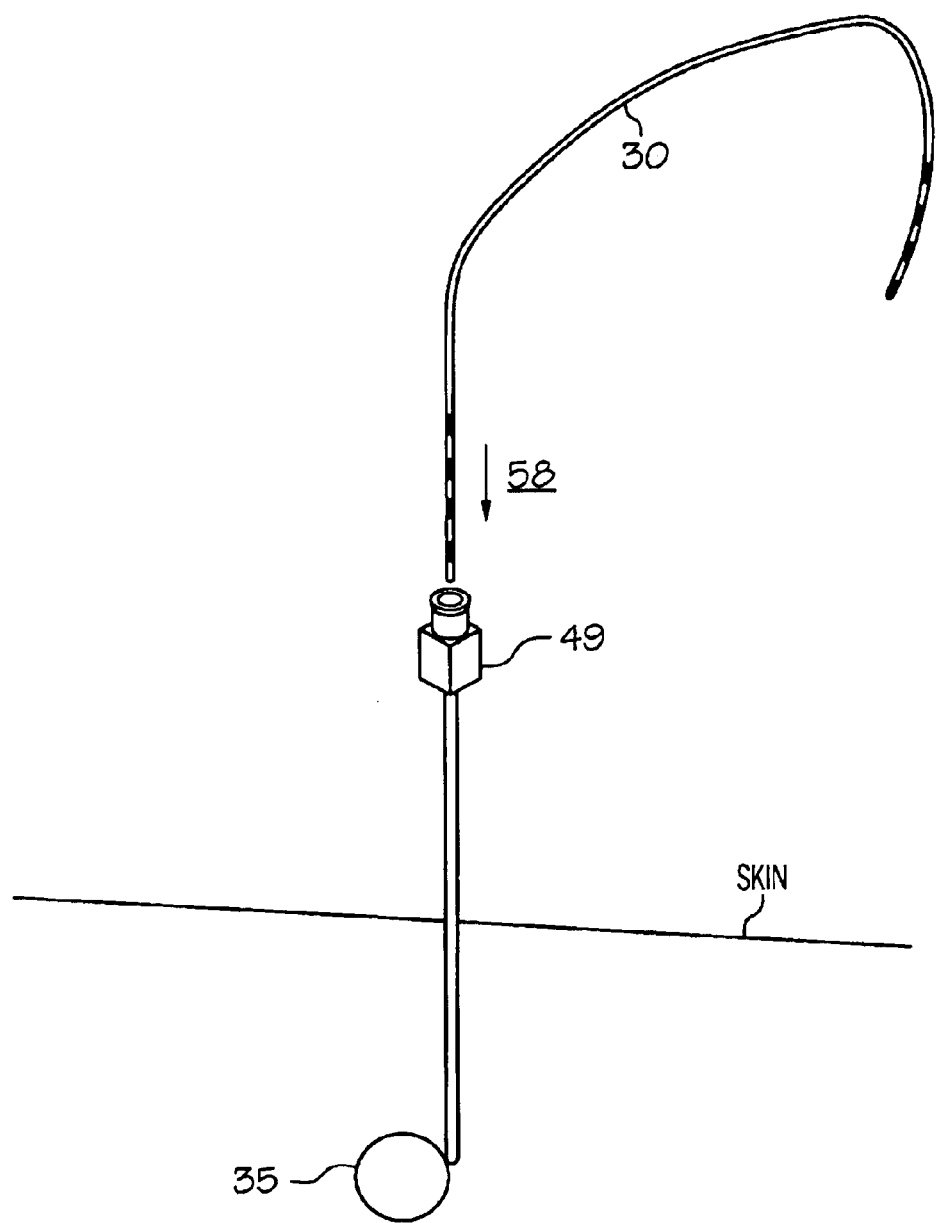
FIG. 9f shows advancing a neurostimulation lead through the dilator sheath lumen to locate the distal neurostimulation electrodes into the foramen and into operative relation with the sacral nerve.

FIG. 9f shows advancing a neurostimulation lead 30 through the dilator sheath lumen to locate the distal neurostimulation electrode(s) into the foramen and into operative relation with the sacral nerve at the desired site 35 in accordance with step 58. The depth marking on the lead body exposed at the proximal dilator sheath hub can be employed to ensure that the lead electrode(s) has exited the dilator sheath distal end but is not advanced too far.

Figure 9G:
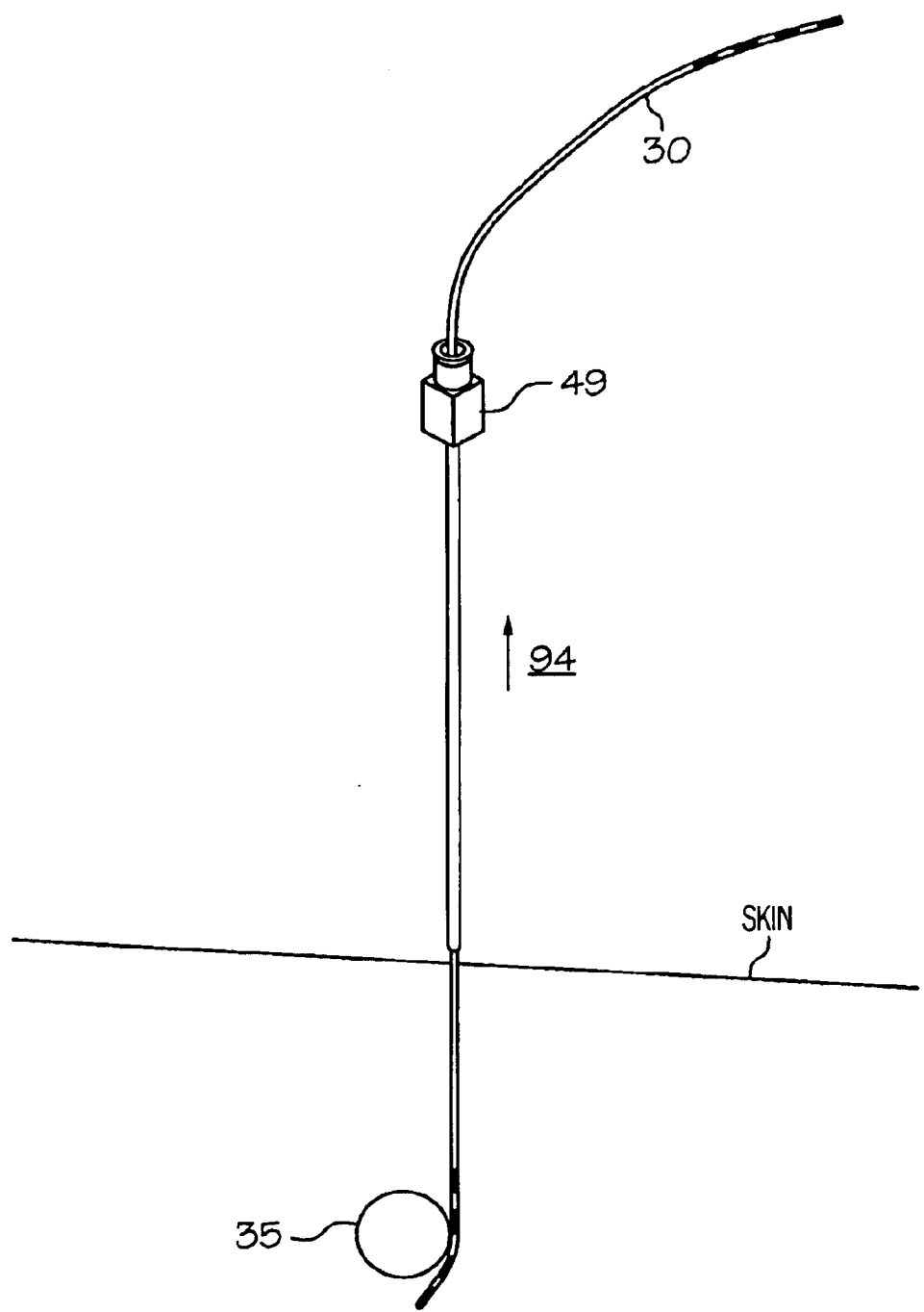
FIG. 9g shows withdrawal of the dilator sheath over the stimulation lead body after electrical testing of the stimulation efficacy.

FIG. 9g shows withdrawal of the dilator sheath 49 over the stimulation lead body after electrical testing of the stimulation efficacy through the lead 30 in accordance with step 94. Then, steps 62, 64 and 66 can be followed as described above to complete the implantation of the neurostimulation lead and implantable neurostimulator. As noted above, step 62 of forming the incision can optionally be performed between steps 52 and 78. Or, step 62 can be performed while the dilator sheath 49 is in place after step 92 or step 58 or FIG. 9a.

FIG. 10 shows a flowchart of a sixth minimally invasive method embodiment employing the dilator 42' of FIGS. 8a–8c along with the needle 36 of FIG. 3a or the foramen needle 38 of FIG. 3d. In this variation, the guide wire 44 is not employed, and needle 36, 38 is either not provided with a hub 45 or the hub 45 is cut off after step 52. The assembled dilator 42' is inserted over the needle 36, 38, in step 90', and the needle is withdrawn in step 56. The remaining steps of FIG. 10 are common with those of FIG. 9a using the instruments as shown in the related illustrations of FIGS. 9b–9g as described above.

Thus, embodiments of a minimally invasive sacral lead implantation instrumentation kits are disclosed with many benefits. Embodiments of the instrumentation kits can reduce patient surgical complications, reduce patient recovery time, and reduce healthcare costs. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A surgical instrumentation kit for minimally invasive implantation of a sacral stimulation lead through a foramen of the sacrum in a patient to electrically stimulate a sacral nerve, the sacral stimulation lead of the type having a lead body extending between a lead body proximal end and a lead body distal end, the lead body having a lead body diameter extending from the lead body proximal end and lead body distal end, the lead body further enclosing at least one electrical conductor extending between at least one proximally located electrical connector adapted to be coupled to an electrical stimulation pulse generator and at least one distally located stimulation electrode adapted to apply electrical stimulation to a sacral nerve, the kit comprising:

a sacral stimulation lead; and a needle having a needle diameter and needle length extending from a needle distal end capable of penetrating body tissue and a needle proximal end, the needle adapted to be grasped by a medical clinician with the needle distal end directed toward and inserted through an entry point of the skin or a skin incision posterior to the sacrum and guided along an insertion path into a foramen to locate at least a distal portion of the needle extending alongside a sacral nerve and a proximal portion of the needle extending from the entry point away from the patient's skin; and a dilator having a dilator body diameter, a dilator body length extending between a dilator proximal end and a dilator distal end, and a dilator body lumen extending from the dilator proximal end to the dilator distal end and having a dilator body lumen diameter sized in operative relation to the lead body diameter and the needle diameter to selectively receive the needle and the lead body therein, wherein the dilator is adapted to be inserted over the needle proximal end to locate the needle within the dilator body lumen and to be advanced distally over the needle through the insertion path to dilate the insertion path to the dilator diameter, the needle is adapted to be withdrawn through the dilator body lumen, the stimulation lead is adapted to be advanced through the dilator body lumen to locate the stimulation lead electrode into operative relation to the sacral nerve, and the dilator is adapted to be withdrawn over the stimulation lead body, wherein if the needle proximal end comprises a hub, the hub is cut off prior to inserting the dilator over the needle proximal end, wherein the needle body comprises depth marks enabling visualization of the depth of insertion of the needle through the insertion path, wherein the dilator body comprises depth marks, and wherein the needle body depth marks correlate to the dilator body depth marks so that the depth of insertion from the skin of both the needle body and the dilator is ascertainable from an exposed needle body depth mark and an exposed dilator body depth mark.

2. The kit as in claim 1, wherein the needle further comprises an electrically conductive needle body providing a distal electrical stimulation electrode end and a proximal electrical connector, the needle body electrically insulated in a region grasped by the medical clinician between the electrical stimulation electrode and electrical connector, whereby the distal needle body location in relation to a sacral nerve can be assessed by delivering electrical stimulation through the needle to evoke a patient response signifying the distal needle body location.

3. The kit as in claim 1, wherein the needle diameter is in the range from about 0.46 mm to about 2.80 mm.

4. The kit as in claim 1, wherein the dilator diameter is in the range from about 0.33 mm to about 4.00 mm.

5. The kit as in claim 1, wherein the needle is selected from the group consisting of a needle without a hub, a needle with a removable hub, a solid rod with a sharp tip, and a foramen needle.

6. The kit as in claim 1, further comprising an anchor selected from the group consisting of a suture anchor and a twist-lock suture anchor for anchoring the stimulation lead to the fascia layer upon withdrawal of the dilator over the stimulation lead body.

7. A surgical instrumentation kit for minimally invasive implantation of a sacral stimulation lead through a foramen of the sacrum in a patient to electrically stimulate a sacral nerve, the sacral stimulation lead of the type having a lead body extending between a lead body proximal end and a lead body distal end, the lead body having a lead body diameter extending from the lead body proximal end and lead body distal end, the lead body further enclosing at least one electrical conductor extending between at least one proximally located electrical connector adapted to be coupled to an electrical stimulation pulse generator and at least one distally located stimulation electrode adapted to apply electrical stimulation to a sacral nerve, the kit comprising:

a sacral stimulation lead; and a needle having a needle diameter and needle length extending from a needle distal end capable of penetrating body tissue and a needle proximal end, the needle adapted to be grasped by a medical clinician with the needle distal end directed toward and inserted through an entry point of the skin or a skin incision posterior to the sacrum and guided along an insertion path into a foramen to locate at least a distal portion of the needle extending alongside a sacral nerve and a proximal portion of the needle extending from the entry point away from the patient's skin; and a dilator having a dilator body diameter, a dilator body length extending between a dilator proximal end and a dilator distal end, and a dilator body lumen extending from the dilator proximal end to the dilator distal end and having a dilator body lumen diameter sized in operative relation to the lead body diameter and the needle diameter to selectively receive the needle and the lead body therein so that the dilator is insertable over the needle proximal end to locate the needle within the dilator body lumen to be capable of being advanced distally over the needle through the insertion path to dilate the insertion path to the dilator diameter and to allow the needle to be withdrawn through the dilator body lumen and to allow the stimulation lead to be advanced through the dilator body lumen to locate the stimulation lead electrode in operative relation to the sacral nerve and to allow the dilator to be withdrawn over the stimulation lead body, wherein if the needle proximal end comprises a hub, the hub is cut off prior to inserting the dilator over the needle proximal end, wherein the needle body comprises depth marks enabling visualization of the depth of insertion of the needle through the insertion path, wherein the dilator body comprises depth marks, and wherein the needle body depth marks correlate to the dilator body depth marks so that the depth of insertion from the skin of both the needle body and the dilator is ascertainable from an exposed needle body depth mark and an exposed dilator body depth mark.

8. The kit as in claim 7, further comprising:

means for creating an incision through the entry point of the epidermis to a fascia layer;

means for anchoring the stimulation lead to the fascia layer upon withdrawal of the dilator over the stimulation lead electrode; and means for closing the incision.

9. The kit as in claim 7, wherein the needle further comprises an electrically conductive needle body providing a distal electrical stimulation electrode and a proximal electrical connector, the needle body electrically insulated in a region grasped by the medical clinician between the electrical stimulation electrode and electrical connector, whereby the distal needle body location in relation to a sacral nerve can be assessed by delivering electrical stimulation through the needle to evoke a patient response signifying the distal needle body location.

10. The kit as in claim 7, wherein the needle diameter is in the range from about 0.46 mm to about 2.80 mm.

11. The kit as in claim 7, wherein the dilator diameter is in the range from about 0.33 mm to about 4.00 mm.

12. The kit as in claim 7, wherein the needle is selected from the group consisting of a needle without a hub, a needle with a removable hub, a solid rod with a sharp tip, and a foramen needle.

13. The kit as in claim 7, further comprising an anchor selected from the group consisting of a suture anchor and a twist-lock suture anchor for anchoring the stimulation lead to the fascia layer upon withdrawal of the dilator over the stimulation lead body.

\* \* \* \* \*